US006274627B1

(12) United States Patent
Lai et al.

(10) Patent No.: US 6,274,627 B1
(45) Date of Patent: Aug. 14, 2001

(54) CONJUGATES OF DITHIOCARBAMATE DISULFIDES WITH PHARMACOLOGICALLY ACTIVE AGENTS AND USES THEREFOR

(75) Inventors: Ching-San Lai, Encinitas; Vassil P. Vassilev, San Diego; Tingmin Wang, San Marcos, all of CA (US)

(73) Assignee: Medinox, Inc., San Diego, CA (US)

( * ) Notice: Subject to any disclaimer, the term of this patent is extended or adjusted under 35 U.S.C. 154(b) by 0 days.

(21) Appl. No.: 09/416,619

(22) Filed: Oct. 12, 1999

(51) Int. Cl.$^7$ ........................ A61K 31/16; A61K 31/095; A61K 31/105
(52) U.S. Cl. ........................... 514/599; 514/706; 514/707
(58) Field of Search ..................... 514/599, 706, 514/707

(56) References Cited

U.S. PATENT DOCUMENTS

| | | |
|---|---|---|
| 4,160,452 | 7/1979 | Theeuwes ........................... 128/260 |
| 4,256,108 | 3/1981 | Theeuwes ........................... 128/260 |
| 4,265,874 | 5/1981 | Bonsen et al. ......................... 424/15 |
| 5,206,264 | 4/1993 | Marangos ............................ 514/483 |
| 5,358,703 | 10/1994 | Lai ........................................ 424/9 |
| 5,373,021 | 12/1994 | Marangos ............................ 514/483 |
| 5,741,815 | * 4/1998 | Lai ...................................... 514/492 |
| 5,756,540 | * 5/1998 | Lai ...................................... 514/492 |
| 5,847,004 | * 12/1998 | Lai ...................................... 514/599 |
| 5,877,203 | 3/1999 | Medford et al. ..................... 514/423 |
| 5,916,910 | * 6/1999 | Lai ...................................... 514/423 |
| 6,093,743 | * 7/2000 | Lai et al. .............................. 514/599 |

FOREIGN PATENT DOCUMENTS

| | | | |
|---|---|---|---|
| WO 97/18805 | 5/1997 | (WO) | ........................ A61K/31/325 |
| WO 97/32585 | 9/1997 | (WO) | ........................ A61K/31/495 |

OTHER PUBLICATIONS

Aisaka et al., "$N^G$–Methylarginine, an Inhibitor of Endothelium–Derived Nitric Oxide Synthesis, is a Potent Pressor Agent in the Guinea Pig: Does Nitric Oxide Regulate Blood Pressure in Vivo?" *Biochemical and Biophysical Research Communications*, 160(2):881–886 (1989).

Atkinson et al., "Cyclosporine–Associated Central Nervous System Toxicity After Allogeneic Bone Marrow Transplantation," *Transplantation*, 38(1):34–37 (1984).

Bredt and Snyder, "Nitric Oxide: A Physiologic Messenger Molecule," *Annu. Rev. Biochem*, 63:175–95 (1994).

Diket et al., "Nitric oxide inhibition causes intrauterine growth retardation and hind–limb disruptions in rats," *Am. J Obstet Gynecol*, 171(5):1243–1250 (1994).

Glauser et al., "Pathogenesis and Potential Strategies for Prevention and Treatment of Septic Shock: An Update," *Clinical Infectious Diseases*, 18(2):S205–16 (1994).

Harbrecht et al., "Inhibition of nitric oxide synthesis during endotoxemia promotes intrahepatic thrombosis and an oxygen radical–mediated hepatic injury," *Journal of Leukocyte Biology*, 52:390–394 (1992).

Henderson et al., "The Effects of Nitric Oxide Inhibition on Regional Hemodynamics During Hyperdynamic Endotoxemia," *Arch. Surg.* 129:1271–1275 (1994).

Hibbs et al., "Evidence for Cytokine–inducible Nitric Oxide Synthesis from L–Arginine in Patients Receiving Interleukin–2 Therapy," *J. Clin. Invest.*, 89:867–877 (1992).

Ingarro, Louis J., "Biosynthesis and Metabolism of Endothelium–Derived Nitric Oxide," *Annu. Rev. Pharmacol. Toxicol.*, 30:535–60 (1990).

Ingarro et al., "Endothelium–derived relaxing factor produced and released from artery and vein is nitric oxide," *Proc. Natl. Acad. Sci. USA*, 84:9265–9269 (1987).

Kim et al., "Loss and Degradation of Enzyme–bound Heme Induced by Cellular Nitric Oxide Synthesis," *Journal of Biological Chemistry*, 270(11):5710–5713 (1995).

Komarov et al., "In Vivo Spin Trapping of Nitric Oxide in Mice," *Biochemical and Biophysical Research Communications*, 195(3):1191–1198 (1993).

Komarov and Lai, "Detection of nitric oxide production in mice by spin–trapping electron paramagnetic resonance spectroscopy," *Biochimica et Biophysica Acta*, 1272:29–36 (1995).

Lai and Komarov, "Spin trapping of nitric oxide produced in vivo in septic–shock mice," *FEBS Letters*, 345:120–124 (1994).

Lowenstein and Snyder, "Nitric Oxide, A Novel Biologic Messenger," *Cell*, 70:705–707 (1992).

Luss et al., "Inhibition of Nitric Oxide Synthesis Enhances the Expression of Inducible Nitric Oxide Synthase mRNA and Protein in a Model of Chronic Liver Inflammation," *Biochemical and Biophysical Research Communications*, 204(2):635–640 (1994).

(List continued on next page.)

Primary Examiner—Kevin E. Weddington
(74) Attorney, Agent, or Firm—Stephen E. Reiter; Foley & Lardner

(57) ABSTRACT

In accordance with the present invention, there are provided conjugates of physiologically compatible free radical scavengers (e.g., dithiocarbamate disulfides (DD)) and pharmacologically active agents (e.g., NSAIDS). Invention conjugates provide a new class of pharmacologically active agents (e.g., anti-inflammatory agents) which cause a much lower incidence of side-effects due to the protective effects imparted by modifying the pharmacologically active agents as described herein. In addition, invention conjugates are more effective than unmodified pharmacologically active agents because cells and tissues contacted by the pharmacologically active agent(s) are protected from the potentially damaging effects of free radical overproduction induced thereby as a result of the co-production of free radical scavenger (e.g., dithiocarbamate), in addition to free pharmacologically active agent, when invention conjugate is cleaved.

9 Claims, 5 Drawing Sheets

OTHER PUBLICATIONS

Miles et al., "Association between biosynthesis of nitric oxide and changes in immunological and vascular parameters in patients treated with interleukin-2," *European Journal of Chemical Investigation*, 24:287–290 (1994).

Minnard et al., "Inhibition of Nitric Oxide Synthesis Is Detrimental During Endotoxemia," *Arch. Surg.*, 129:142–148 (1994).

Mitaka et al., "Effects of nitric oxide synthase inhibitor on hemodynamic change and $O_2$ delivery in septic dogs," *Inhibitor of No Synthase and Endotoxin Shock*, H2017–H2020 (1995).

Moncada and Higgs, "The L–Arginine–Nitric Oxide Pathway," *The New England Journal of Medicine*, 329(27):2002–2012 (1993).

Nieper et al., "The development and examination of fungistatic compounds for cancer treatment" Aerztl. Forsh., 16:I/523–I/540 (1962).

Richard M. J. Palmer, "The Discovery of Nitric Oxide in the Vessel Wall," *Arch. Surg.*, 128:396–401 (1993).

Palmer et al. "Nitric oxide release accounts for the biological activity of endothelium–derived relaxing factor," *Nature*, 327:524–526 (1987).

Radomski and Moncada, "Regulation of Vascular Homeostasis by Nitric Oxide" *Thrombosis and Haemostasis*, 70(1):36–41 (1993).

Rees et al., "Role of endothelium–derived nitric oxide in the regulation of blood pressure," *Proc. Natl. Acad. Sci. USA* ., 86:3375–3378 (1989).

Robertson et al., "Detrimental Hemodynamic Effects of Nitric Oxide Synthase Inhibition in Septic Shock," *Arch Surg* 129:149–156 (1994).

Rodenberg et al., "Nitric Oxide: An Overview," *The American Journal of Surgery*, 170:292–303 (1995).

Shinobu et al., "Sodium N–Methyl–D–glucamine Dithiocarbamate and Cadmium Intoxication," *Acta pharmacol, et toxicol*, 54:189–194 (1984).

Statman et al., "Nitric Oxide Inhibition in the Treatment of the Sepsis Syndrome Is Detrimental to Tissue Oxygenation," *Journal of Surgical Research*, 57(1):93–98 (1994).

St. John and Dorinsky, "Immunologic Therapy for ARDS, Septic Shock and Multiple–Organ Failure," *Chest*, 103:932–943 (1993).

Waage et al., "Cytokine mediators of septic infections in the normal and granulocytopenic host," *Eur J Haematol.*, 50:243–249 (1993).

Winlaw et al., "Urinary Nitrate Excretion is a Noninvasive Indicator of Acute Cardiac Allograft Rejection and Nitric Oxide Production in the Rat," *Transplantation*, 58(9):1031–1036 (1994).

Yang et al., "Induction of Myocardial Nitric Oxide Synthase by Cardiac Allograft Rejection," *J. Clin. Invest.*, 94:714–721 (1994).

Graham et al., "Nonsteroidal anti–inflammatory effect of sulindac sulfoxide and sulfide on gastric mucosa," *Clin. Pharmacol. Ther.*, 38:65–70 (1985).

Carson et al., "The Relative Gastrointesinal Toxicity of the Nonsteroidal Anti–imflammatory Drugs," *Arch Intern Med*, 147:1054–1059 (1987).

Glaser et al., "Etodolac selectively inhibits human prostaglandin G/H synthase 2 (PGHS–2) versus human PGHS–1," *European Journal of Pharmacology*, 281:107–111 (1995).

Whittle et al., "Induction of nitric oxide synthase and microvascular injury in the rat jejunum provoked by indomethacin," *British Journal of Pharmacology* 116:2286–2290 (1995).

Middleton et al., "Increased nitric oxide synthesis in ulcerative colitis," *The Lancet*, 341:465–466 (1993).

* cited by examiner

CONJUGATES OF DITHIOCARBAMATE DISULFIDES WITH PHARMACOLOGICALLY ACTIVE AGENTS AND USES THEREFOR

RELATED APPLICATIONS

This application claims priority from PCT Application No. PCT/US98/10295 (Published as WO98/55453), now pending, and U.S. Ser. No. 09/103,639, filed Jun. 23, 1998, now pending.

FIELD OF THE INVENTION

The present invention relates to novel conjugated forms of pharmacologically active agents, and methods for the preparation and use thereof. In a particular aspect of the invention, methods are provided for simultaneously treating a pathological condition with a pharmacologically active agent and reducing free radical levels.

BACKGROUND OF THE INVENTION

Despite the advent of modern pharmaceutical technology, many drugs still possess untoward toxicities which often limit the therapeutic potential thereof. For example, although Non-Steroid Anti-Inflammatory Drugs (NSAIDs) are a class of compounds which are widely used for the treatment of inflammation, pain and fever, NSAIDs (e.g., aspirin, ibuprofen and ketoprofen) can cause gastrointestinal ulcers, a side-effect that remains the major limitation to the use of NSAIDs (see, for example, J. L. Wallace, in Gastroenterol. 112:1000–1016 (1997); A. H. Soll et al., in Ann Intern Med. 114:307–319 (1991); and J. Bjarnason et al., in Gastroenterol. 104:1832–1847 (1993)).

There are two major ulcerogenic effects of NSAIDs: (1) topical irritant effects on the epithelium of the gastrointestinal tract and (2) suppression of gastrointestinal prostaglandin synthesis. In recent years, numerous strategies have been attempted to design and develop new NSAIDs that reduce the damage to the gastrointestinal tract. These efforts, however, have largely been unsuccessful. For example, enteric coating or slow-release formulations designed to reduce the topical irritant properties of NSAIDs have been shown to be ineffective in terms of reducing the incidence of clinically significant side effects, including perforation and bleeding (see, for example, D. Y. Graham et al., in Clin. Pharmacol. Ther. 38:65–70 (1985); and J. L. Carson, et al., in Arch. Intern. Med., 147:1054–1059 (1987)).

It is well recognized that aspirin and other NSAIDs exert their pharmacological effects through the inhibition of cyclooxygenase (COX) enzymes, thereby blocking prostaglandin synthesis (see, for example, J. R. Van in Nature, 231:232–235 (1971)). There are two types of COX enzymes, namely COX-1 and COX-2. COX-1 is expressed constitutively in many tissues, including the stomach, kidney, and platelets, whereas COX-2 is expressed only at the site of inflammation (see, for example, S. Kargan et al. in Gastroenterol., 111:445–454 (1996)). The prostagladins derived from COX-1 are responsible for many of the physiological effects, including maintenance of gastric mucosal integrity.

Many attempts have been made to develop NSAIDs that only inhibit COX-2, without impacting the activity of COX-1 (see, for example, J.A. Mitchell et al., in Proc. Natl. Acad. Sci. USA 90:11693–11697 (1993); and E. A. Meade et al., in J. Biol. Chem., 268:6610–6614 (1993)). There are at least two NSAIDs presently on the market (i.e., nabumetone and etodolac) that show marked selectivity for COX-2 (see, for example, E. A. Meade, supra.; and K. Glaser et al., in Eur. J. Pharmacol. 281:107–111 (1995)). These drugs appear to have reduced gastrointestinal toxicity relative to other NSAIDs on the market.

On the basis of encouraging clinical as well as experimental data, the development of highly selective COX-2 inhibitors appears to be a sound strategy to develop a new generation of anti-inflammatory drugs. However, the physiological functions of COX-1 and COX-2 are not always well defined. Thus, there is a possibility that prostagladins produced as a result of COX-1 expression may also contribute to inflammation, pain and fever. On the other hand, prostagladins produced by COX-2 have been shown to play important physiological functions, including the initiation and maintenance of labor and in the regulation of bone resorption (see, for example, D. M. Slater et al., in Am. J. Obstet. Gynecol., 172:77–82 (1995); and Y. Onoe et al., in J. Immunol. 156:758–764 (1996)), thus inhibition of this pathway may not always be beneficial. Considering these points, highly selective COX-2 inhibitors may produce additional side effects above and beyond those observed with standard NSAIDs, therefore such inhibitors may not be highly desirable.

Since anthracyclines such as adriamycin are commonly used antitumor agents, considerable efforts have also been made to develop strategies for reducing the acute and delayed cardiomyopathies induced by anthracyclines, while maintaining the therapeutic efficacy of these compounds. The molecular mechanism of cardiomyopathy is now attributed to the adriamycin-induced release of iron from intracellular iron proteins, resulting in the formation of an adriamycin-iron complex. The adriamycin-iron complex generates reactive oxygen species, causing the scission and condensation of DNA, peroxidation of phospholipid membranes, depletion of cellular reducing equivalents, interference with mitochondrial respiration, and disruption of cell calcium homeostasis (see, for example, Myers et al., in Science 197:165–167 (1977); and Gianni et al., in Rev. Biochem. Toxicol. 5:1–82 (1983)). In addition to cardiomyopathy, adriamycin administration causes cutaneous irritation and alopecia, mucositis (stomatitis and esophagitis), phlebosclerosis and hematologic toxicities and many other local and systemic toxicities.

Recently, ICRF-187 (i.e., dexrazoxane) has been demonstrated to be effective for the removal of iron from the anthracycline-iron complex, therefore preventing the cardiac toxicity in cancer patients receiving adriamycin chemotherapy (see, for example, Kolaric et al., in Oncology 52:251–5 (1995)). However, when chelated with iron, the iron-ICRF-187 complex per se is also very effective at promoting hydroxyl radical generation via the Fenton reaction, causing oxidative damage to tissues (see, for example, Thomas et al., in Biochem. Pharmacol., 45:1967–72 (1993)). In addition, since ICRF-187 is a strong chelator (having a structure similar to EDTA), it chelates not only low-molecular-weight iron, but also chelates iron from transferrin and ferritin, as well as copper from ceruloplasmin, thus potentially affecting normal cellular iron metabolism.

Accordingly, there is still a need in the art for modified forms of NSAIDs, and other pharmacologically active agents, which cause a reduced incidence of side-effects, relative to the incidence of side-effects caused by such pharmacologically active agents as aspirin, ibuprofen, and the like.

BRIEF DESCRIPTION OF THE INVENTION

In accordance with the present invention, there are provided conjugates of physiologically compatible free radical scavengers (e.g., dithiocarbamate disulfides (DD)) and pharmacologically active agents (e.g., NSAIDs). Invention conjugates provide a new class of pharmacologically active agents (e.g., anti-inflammatory agents) which cause a much lower incidence of side-effects due to the protective effects imparted by modifying the pharmacologically active agents as described herein.

Recent evidence has shown that NSAID administration up-regulates the expression of inducible nitric oxide synthase (see, for example, B. J. R. Whittle et al., in Br. J. Pharmacol., 116:2286–2290 (1995)). Excessive nitric oxide produced from inducible nitric oxide synthase is known to contribute to the generation of mucosal damage (see, for example, S. J. Middleton et al., in Lancet 341:456–466 (1993); and M. J. S. Miller et al., in Scand. J. Gastroenterol., 264:11–16 (1993)). When chelated with iron (e.g., intracellular iron), nitric oxide scavengers (such as a dithiocarbamate-iron complex) becomes an effective nitric oxide scavenger which binds tightly to nitric oxide and reduces in vivo nitric oxide levels. It is now recognized that excessive nitric oxide production can induce the expression of COX-2, thereby enhancing the cascade of inflammatory reactions. Thus, scavenging NO by a nitric oxide scavenger (such as the dithiocarbamate-iron complex) could reduce the negative consequences brought about by excessive COX-2 levels, by reducing the expression of COX-2.

In summary, there are a number of advantages of conjugates according to the invention (e.g., DD-NSAID), including:

(i) reduced topical irritant effects of NSAIDs, (ii) enhanced tissue delivery of both drugs as a result of a decrease in net charges on the molecule, particularly for acidic NSAIDs such as aspirin, diclofenac and ibuprofen, thereby reducing the quantity of material which must be delivered to achieve an effective dosage, (iii) chelating intracellular free iron ions, thereby preventing iron-related oxidative damage, (iv) inhibiting VCAM-1 expression, thereby blocking neutrophil adherence to the vascular endothelium induced by NSAID administration, and (v) scavenging free radicals such as intracellular nitric oxide, thereby preventing the production of peroxynitrite (and/or scavenging any peroxynitrite that may be formed), a potent oxidant, and reducing the induction of COX-2 expression, which could induce further inflammatory response.

In another aspect of the invention, there are described bio-cleavable conjugates of a suitable free radical scavenger (e.g., dithiocarbamate disulfide) and an anti-neoplastic agent (e.g., adriamycin, wherein the resulting conjugate is referred to as DD-adriamycin), which alleviate some of the toxicities associated with administration of anti-neoplastics such as adriamycin. There are a number of advantages of DC-adriamycin over adriamycin alone, including:

(i) reducing cutaneous irritation and alopecia and vascular damage (because the conjugates are inactive until they have reached the intracellular site of action), (ii) chelating intracellular iron, thus reducing free radical-induced acute and delayed cardiomyopathies, and (iii) removing excessive free radicals (such as nitric oxide) produced from malignant and cancerous tissues.

The decline of plasma naproxen following PDD-Naproxen administration was monophonic. Note the lower plasma $C_{max}$ shown for PDD-Naproxen.

Figure 5:
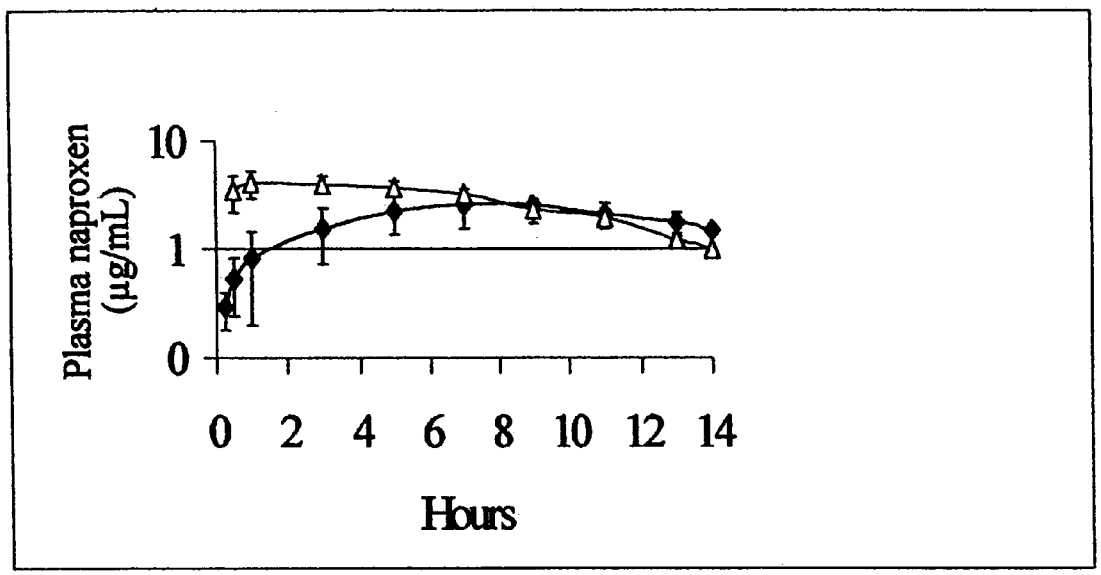

FIG. 5 presents concentration versus time curves for naproxen following oral administration of naproxen or PDD-Naproxen. Open triangles represent plasma concentration of naproxen following oral administration of 2.2 mg/kg of naproxen and blackened rectangles represent plasma concentration of naproxen following oral administration of 4 mg/kg of PDD-Naproxen. Following oral administration of PDD-Naproxen, the time to maximum concentration of naproxen in plasma was considerably longer compared to naproxen administration ($T_{max}$ of 6.4 and 1.3 hours for PDD-Naproxen and naproxen, respectively). The corresponding $C_{max}$ values were 2.34 and 4.82 μg/mL for PDD-Naproxen and naproxen, respectively. There was no significant difference for $AUC_{nif}$ values.

DETAILED DESCRIPTION OF THE INVENTION

In accordance with the present invention, there are provided compounds comprising a suitable free radical scavenger (e.g., a dithiocarbamate disulfide) covalently attached to a pharmacologically active agent.

Dithiocarbamates such as pyrrolidine dithiocarbamate are potent inhibitors of nuclear factor kappa B in intact cells (see, for example, R. Schreck et al., in J. Exp. Med., 175:1181–1194 (1992)). In addition, nuclear factor kappa B has been shown to up-regulate the expression of cell adhesive molecules, including the vascular cell adhesive molecule 1 (VCAM-1; see, for example, M. F. Iademarco et al., in J. Biol. Chem., 267:16323–16329 (1992)). Endothelial expression of VCAM-1 causes the adherence of neutrophils to the endothelium, an early event leading to inflammation and subsequent vascular damage and reduction of blood flow (see, for example, M. N. Oppenheimer et al., in J. Immunol., 147:42207–4210 (1991)). It has been recognized that NSAID administration increases neutrophil adherence to the vascular endothelium in the gastric and mesenteric microcirculation (see, for example, J. L. Wallace et al., in Gastroenterol., 105:1630–1636 (1993); and H. Asako et al., in Am J. Physiol., 262:G903-G908 (1992)). Therefore, conjugates of NSAIDs with dithiocarbamate disulfides would block VCAM-1 expression, thereby avoiding the vascular problems associated with neutrophil adherence to the endothelium.

$$R_1R_2N\text{---}C(S)\text{---}S\text{---}S\text{---}(S)C\text{---}NR_2R_1 \quad (1)$$

wherein:
  each $R_1$ and $R_2$ is independently selected from a $C_1$ up to $C_{18}$ alkyl, substituted alkyl, cycloalkyl, substituted cycloalkyl, heterocyclic, substituted heterocyclic, alkenyl, substituted alkenyl, alkynyl, substituted alkynyl, aryl, substituted aryl, heteroaryl, substituted heteroaryl, alkylaryl, substituted alkylaryl, arylalkyl, substituted arylalkyl, arylalkenyl, substituted arylalkenyl, arylalkynyl, substituted arylalkynyl, aroyl, substituted aroyl, acyl, substituted acyl, or
  $R_1$ and $R_2$ can cooperate to form a 5-, 6- or 7-membered ring including N, $R_1$ and $R_2$, or
  $R_1$ or $R_2$ is a divalent moiety selected from the group consisting of alkylene, substituted alkylene, oxyalkylene, substituted oxyalkylene, alkenylene, substituted alkenylene, arylene, substituted arylene, alkarylene, substituted alkarylene, aralkylene and substituted aralkylene, wherein said divalent moiety serves as the same substituent for two dithiocarbamate structures, thereby linking said structures together so as to form a bis(dithiocarbamate) species, except for disulfide derivatives of diethyldithiocarbamate and those disulfide derivatives disclosed in H. A. Nieper et al., Aerztl. Forsh. 16:I/523-I/540 (1962) (in german), which is incorporated herein in its entirety by reference.

Presently preferred compounds having generic structure I are those wherein:
  each of $R_1$ and $R_2$=a $C_1$ up to $C_{12}$ alkyl, substituted alkyl, alkenyl, substituted alkenyl, alkynyl or substituted alkynyl, wherein the substituents are selected from carboxyl, —C(O)H, oxyacyl, phenol, phenoxy, pyridinyl, pyrrolidinyl, amino, amido, hydroxy, nitro or sulfuryl.

Especially preferred compounds having generic structure I are those wherein:
  $R_1$ is selected from a $C_2$ up to $C_8$ alkyl or substituted alkyl, wherein the substituents are selected from carboxyl, acetyl, pyridinyl, pyrrolidinyl, amino, amido, hydroxy or nitro, and
  $R_2$ is selected from a $C_1$ up to $C_6$ alkyl or substituted alkyl, or $R_2$ cooperates with $R_1$ to form a 5-, 6- or 7-membered ring including N, $R_2$ and $R_1$.

The presently most preferred compounds having generic structure I are those wherein:
  $R_1$ is selected from a $C_2$ up to $C_8$ alkyl or substituted alkyl, wherein the substituents are selected from carboxyl, acetyl, amido or hydroxy, and
  $R_2$ is selected from a $C_1$ up to $C_4$ alkyl or substituted alkyl.

When $R_1$ and $R_2$ cooperate to form a 5-, 6- or 7-membered ring, the combination of $R_1$ and $R_2$ can be a variety of saturated or unsaturated 4, 5 or 6 atom bridging species selected from alkenylene or —O—, —S—, —C(O)— and/or —N(R)-containing alkylene moieties, wherein R is hydrogen or a lower alkyl moiety.

As employed herein, "substituted alkyl" comprises alkyl groups further bearing one or more substituents selected from hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, —C(O)H, acyl, oxyacyl, carboxyl, carbamate, sulfonyl, sulfonamide, sulfuryl, and the like.

As employed herein, "cycloalkyl" refers to cyclic ring-containing groups containing in the range of about 3 up to 8 carbon atoms, and "substituted cycloalkyl" refers to cycloalkyl groups further bearing one or more substituents as set forth above.

As employed herein, "alkenyl" refers to straight or branched chain hydrocarbyl groups having at least one carbon-carbon double bond, and having in the range of about 2 up to 12 carbon atoms, and "substituted alkenyl" refers to alkenyl groups further bearing one or more substituents as set forth above.

As employed herein, "alkynyl" refers to straight or branched chain hydrocarbyl groups having at least one carbon-carbon triple bond, and having in the range of about 2 up to 12 carbon atoms, and "substituted alkynyl" refers to alkynyl groups further bearing one or more substituents as set forth above.

As employed herein, "aryl" refers to aromatic groups having in the range of 6 up to 14 carbon atoms and "substituted aryl" refers to aryl groups further bearing one or more substituents as set forth above.

As employed herein, "alkylaryl" refers to alkyl-substituted aryl groups and "substituted alkylaryl" refers to alkylaryl groups further bearing one or more substituents as set forth above.

As employed herein, "arylalkyl" refers to aryl-substituted alkyl groups and "substituted arylalkyl" refers to arylalkyl groups further bearing one or more substituents as set forth above.

As employed herein, "arylalkenyl" refers to aryl-substituted alkenyl groups and "substituted arylalkenyl" refers to arylalkenyl groups further bearing one or more substituents as set forth above.

As employed herein, "arylalkynyl" refers to aryl-substituted alkynyl groups and "substituted arylalkynyl" refers to arylalkynyl groups further bearing one or more substituents as set forth above.

As employed herein, "aroyl" refers to aryl-carbonyl species such as benzoyl and "substituted aroyl" refers to aroyl groups further bearing one or more substituents as set forth above.

As employed herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As employed herein, "acyl" refers to alkyl-carbonyl species.

As employed herein, "halogen" refers to fluoride, chloride, bromide or iodide atoms.

Diseases and conditions contemplated for treatment in accordance with the present invention include inflammatory and infectious diseases, such as, for example, septic shock, hemorrhagic shock, anaphylactic shock, toxic shock syndrome, ischemia, cerebral ischemia, administration of cytokines, overexpression of cytokines, ulcers, inflammatory bowel disease (e.g., gastritis, ulcerative colitis or Crohn's disease), diabetes, arthritis, asthma, Alzheimer's disease, Parkinson's disease, multiple sclerosis, cirrhosis, allograft rejection, encephalomyelitis, meningitis, pancreatitis, peritonitis, vasculitis, lymphocytic choriomeningitis, glomerulonephritis, ophthalmologic diseases (e.g., uveitis, glaucoma, blepharitis, chalazion, allergic eye disease, corneal ulcer, keratitis, cataract, retinal disorders, age-related macular degeneration, optic neuritis, and the like), ileitis, inflammation (e.g., liver inflammation, renal inflammation, airway inflammation, and the like), burn, infection (including bacterial (e.g., E.coli infection), viral (e.g., HIV), fungal (e.g., Candidiosis and histoplasmosis and parasitic (e.g., Leishmaniasis and Schistosomiasis) infections), hemodialysis, chronic fatigue syndrome, stroke, cancers (e.g., breast, melanoma, carcinoma, and the like), cardiovascular diseases associated with overproduction of inflammatory cytokines (e.g., heart disease, cardiopulmonary bypass, ischemic/reperfusion injury, and the like), ischemic/reperfusion associated with overproduction of inflammatory cytokines, adult respiratory distress syndrome, cachexia, myocarditis, autoimmune disorders, eczema, psoriasis, heart failure, heart disease, atherosclerosis, dermatitis, urticaria, systemic lupus erythematosus, AIDS, AIDS dementia, neurodegenerative disorders (e.g., chronic neurodegenerative disease), chronic pain, priapism, cystic fibrosis, amyotrophic lateral sclerosis, schizophrenia, depression, premenstrual syndrome, anxiety, addiction, migraine, Huntington's disease, epilepsy, gastrointestinal motility disorders, obesity, hyperphagia, solid tumors (e.g., neuroblastoma), malaria, hematologic cancers, myelofibrosis, lung injury, graft-versus-host disease, head injury, CNS trauma, hepatitis, renal failure, liver disease (e.g., chronic hepatitis C), drug-induced lung injury (e.g., paraquat), myasthenia gravis (MG), transplant rejection and preservation, fertility enhancement, bacterial translocation, circulatory shock, traumatic shock, alcohol hang-over, and the like.

Treatment of such conditions can be carried out with a variety of reagents, such as, for example, inhibitors of cytokine synthesis/release (e.g., anti-cytokine antibodies, anti-cytokine receptor antibodies, and the like), anti-endotoxin antibodies, bradykinin antagonists, synthetic peptide blocking bradykinin receptors, bactericidal/permeability increasing protein, inhibitors of the coagulation cascade (e.g., antibodies to platelet activating factor), inhibitors of complement activation, inhibitors of arachidonate metabolism, inhibitors of nitric oxide synthase enzymes, immunosuppressors, diabetic therapeutic agents, anti-inflammatories, agents useful for stroke therapy, agents useful for asthma therapy, agents useful for cirrhosis therapy, anti-cancer therapeutics, anti-microbial therapeutics, anti-fungal therapeutics, anti-retroviral therapeutics, agents useful for the treatment of opportunistic infections and malignancies, agents useful for the treatment of Lupus erythmatosus, agents useful for the treatment of uveitis, thrombolytic agents, antispasmodic agents, antidiarrheal agents, agents useful for the treatment of constipation, antihistamines, agents useful for the treatment of Parkinson's disease, therapeutic agents for Crohn's disease therapy, anti-oxidants, and the like.

Thus, pharmacologically active agents contemplated for modification in accordance with the present invention include:

NSAIDs, such as acetaminophen (Tylenol, Datril, etc.), aspirin, ibuprofen (Motrin, Advil, Rufen, others), choline magnesium salicylate (Triasate), choline salicylate (Anthropan), diclofenac (voltaren, cataflam), diflunisal (dolobid), etodolac (Iodine), fenoprofen calcium (nalfon), flurobiprofen (ansaid), indomethacin (indocin, indometh, others), ketoprofen (orudis, oruvail), ketorolac tromethamine (toradol), magnesium salicylate (Doan's, magan, mobidin, others), meclofenamate sodium (meclomen), mefenamic acid (relafan), oxaprozin (daypro), piroxicam (feldene), sodium salicylate, sulindac (clinoril), tolmetin (tolectin), meloxicam, nabumetone, naproxen, lornoxicam, nimesulide, indoprofen, remifenzone, salsalate, tiaprofenic acid, flosulide, and the like;

analgesics/antipyretics (e.g., aspirin, acetaminophen, ibuprofen, naproxen sodium, buprenorphine hydrochloride, propoxyphene hydrochloride, propoxyphene napsylate, meperidine hydrochloride, hydromorphone hydrochloride, morphine sulfate, oxycodone hydrochloride, codeine phosphate, dihydrocodeine bitartrate, pentazocine hydrochloride, hydrocodone bitartrate, levorphanol tartrate, diflunisal, trolamine salicylate, nalbuphine hydrochloride, mefenamic acid, butorphanol tartrate, choline salicylate, butalbital, phenyltoloxamine citrate, diphenhydramine citrate, methotrimeprazine, cinnamedrine hydrochloride, meprobamate, and the like);

sedatives/hypnotics (e.g., barbiturates (e.g., pentobarbital, pentobarbital sodium, secobarbital sodium), benzodiazapines (e.g., flurazepam hydrochloride, triazolam, tomazeparm, midazolam hydrochloride, and the like);

antianginal agents (e.g., beta-adrenergic blockers, calcium channel blockers (e.g., nifedipine, diltiazem hydrochloride, and the like), nitrates (e.g., nitroglycerin, isosorbide dinitrate, pentaerythritol tetranitrate, erythrityl tetranitrate, and the like));

antianxiety agents (e.g., lorazepam, buspirone hydrochloride, prazepam, chlordiazepoxide hydrochloride, oxazepam, clorazepate dipotassium, diazepam, hydroxyzine pamoate, hydroxyzine hydrochloride, alprazolam, droperidol, halazepam, chlormezanone, and the like);

antidepressants (e.g., doxepin hydrochloride, amoxapine, trazodone hydrochloride, amitriptyline hydrochloride, maprotiline hydrochloride, phenelzine sulfate, desipramine hydrochloride, nortriptyline hydrochloride, tranylcypromine sulfate, fluoxetine hydrochloride, doxepin hydrochloride, imipramine hydrochloride, imipramine pamoate, nortriptyline, amitriptyline hydrochloride, isocarboxazid, desipramine hydrochloride, trimipramine maleate, protriptyline hydrochloride, and the like);

antipsychotic agents (e.g., haloperidol, loxapine succinate, loxapine hydrochloride, thioridazine, thioridazine hydrochloride, thiothixene, fluphenazine hydrochloride, fluphenazine decanoate, fluphenazine enanthate, trifluoperazine hydrochloride, chlorpromazine hydrochloride, perphenazine, lithium citrate, prochlorperazine, and the like);

antimanic agents (e.g., lithium carbonate), antiarrhythmics (e.g., bretylium tosylate, esmolol hydrochloride, verapamil hydrochloride, amiodarone, encainide hydrochloride, digoxin, digitoxin, mexiletine hydrochloride, disopyramide phosphate, procainamide hydrochloride, quinidine sulfate, quinidine gluconate, quinidine polygalacturonate, flecainide acetate, tocainide hydrochloride, lidocaine hydrochloride, and the like);

antihypertensive drugs, such as diuretics (hydrochlorothiazide, chlorthalidone, metolazone, indapamide, furosemide, bumetanide, torsemide, triamterene, amiloride, spronolactone), beta-adrenergic blocking agents (acebutolol, atenolol, betaxolol, cartelol, labetalol, metoprolol, nadolol, penbutolol, pindolol, propranolol, timolol), angiotensin converting enzyme inhibitors (benazepril, captopril, enalapril, fosinopril, quinoapril, ramimpril, losartan), calcium channel-blocking agents (diltiazem, verapamil, amlodipine, felodipine, isradipine, nicardipine, nifedipine), aplha-adrenoceptor blocking agents, sympatholytics, and vasodilators (such as prazosin, terazosin, doxazosin, clonidine, guanabenz, guanfacine, methylodopa, guanethidine, guanethidine monosulfate, reserpine, hydralazine, minoxidil, and the like), as well as agents such as trimethaphan camsylate, phenoxybenzamine hydrochloride, pargyline hydrochloride, deserpidine, diazoxide, rescinnamine, sodium nitroprusside, rauwolfia serpentina, alseroxylon, phentolamine mesylate, and the like;

antihistamine/antipruritic drugs, such as ethanolamines (e.g., diphenhydramine, diphenhydramine hydrochloride, clemastine, clemastine fumarate, and the like), ethylenediamines (e.g., brompheniramine, brompheniramine maleate, chlorpheniramine, chlorpheniramine maleate, dexchlorpheniramine maleate, triprolidine, triprolidine hydrochloride, and the like), phenothiazines (e.g., promethazine), piperidines (e.g., hydroxzine, hydroxyzine hydrochloride, terfenadine, astemizole, azatadine, azatadine maleate, and the like), cyproheptadine, cyproheptadine hydrochloride, loratidine, carbinoxamine maleate, diphenylpyraline hydrochloride, phenindamine tartrate, tripelennamine hydrochloride, methdilazine hydrochloride, trimprazine tartrate, and the like;

immunosuppressants, such as glucocorticoids (methylprednisolone), myelin basic protein (e.g., 7-capaxone), anti-Fc receptor monoclonal antibodies, hydroorotate dehydrogenase inhibitor, anti-IL2 monoclonal antibodies (e.g., CHI-621 and dacliximab), buspirone, castanospermine, CD-59 (complement factor inhibitor), 5-lipoxygenase inhibitor (e.g., CMI-392), phosphatidic acid synthesis antagonists, ebselen, edelfosine, enlimomab, galaptin, platelet activating factor antagonists, selectin antagonists (e.g., ICAM-4), interleukin-10 agonist, macrocylic lactone, methoxatone, mizoribine, OX-19, peptigen agents, PG-27, protein kinase C inhibitors, phosphodiesterase IV inhibitor, single chain antigen binding proteins, complement factor inhibitor, sialophorin, sirolimus, spirocyclic lactams, 5-hydroxytryptamine antagonist, anti-TCR monoclonal antibodies, CD5 gelonin and TOK-8801, and the like;

antimetabolite cytotoxics (azathioprine, cyclophosphamide), C5a release inhibitor, benzydamine, peldesine, pentostatin, SDZ-ASM-981, thalidomide, benzoporphyrin derivatives, arachidonate antagonists (e.g., halometasone, halobetasol propionate), corticosteriod (clobetasol propionate), growth hormone antagonists (octapeptide somatostatin analogue, lanreotide, angiopeptin and dermopeptin), thymopentin, and the like;

neuroprotective agents, such as a-adrenoreceptor antagonist (i.e, α-dihydroergocryptine), NMDA antagonists (e.g., 5,6,7-tichloro-THQTQ, remacemide, 2-piperazinecarboxylic acid, N-indologlycinamide derivatives, spiro[benzo(b)thiophen-4(5H) derivatives, CP-101606, eliprodil, dexanabinol, GV-150526, L-695902, L-701324, amantadine derivatives, dizocilpine, benzomorphan derivatives, aptiganel, (S)-α-phenyl-2-pyridine ethanamide dihyrochloride and 1-amino-cyclopentanecarboxylic acid), sodium channel antagonists (e.g., 619C89), glycine antagonists (e.g., glystasins), calcium channel antagonists (e.g., 3,5-pyridinedicarboxylic acid derivatives, conopeptides, 1-piperazineethanol, thieno[2,3-b]pyridine-5-carboxylic acid derivatives, NS-3034, nilvadipine, nisoldipine, tirilazad mesylate, 2H-1-enzopyran-6-ol, nitrone spin traps, iacidipine, iomeerzine hydrochloride, lemildipine, lifarizine, CPC-304, efonidipine, F-0401, piperazine derivatives), calpain inhibitors, fibrinogen antagonists (e.g., ancrod), integrin antagonists (e.g., antegren), thromboxane $A_2$ antagonist (e.g., 9H-carbazole-9-propanoic acid derivatives, 5-Heptenoic acid derivatives and 1-azulenesulfonic acid derivatives), brain-derived neurotropic factor, adrenergic transmitter uptake inhibitor (e.g., 1-butanamine), endothelin A receptor antagonists (e.g., benzenesulfonamide derivatives, GABA A receptor antagonists (e.g., triazolopyrimidine derivatives and cyclohexaneacetic acid derivatives), GPIIb IIIa receptor antagonists (e.g., C68-22), platelet aggregation antagonist (e.g., 2(1H)-quinolinone derivatives, 1H-pyrrole-1-acetic acid derivatives and coumadin), Factor Xa inhibitor, CPC-211, corticotropin releasing factor agonist, thrombin inhibitor (e.g., cothrombins, fraxiparine, dermatan sulfate and heparinoid), dotarizine, intracellular calcium chelators (e.g., BAPTA derivatives), radical formation antagonists (EPC-K1, 3-pyridinecarboxamide derivatives, superoxide dismutase, raxofelast, lubeluzole, 3H-pyrazol-3-one derivatives, kynurenic acid derivatives, homopiperazine derivatives, and polynitroxyl albumin), protein kinase inhibitors (e.g., 1H-1,4-diazepine), nerve growth agonist (e.g., floor plate factor-5), glutamate antagonist (e.g., cyclohexanepropanoic acid, riluzole, NS-409 and acetamide derivatives), lipid peroxidase inhibitor (e.g., 2,5-cyclohexadiene-1,4-dione derivatives), sigma receptor agonist (e.g., cyclopropanemethanamine derivatives and SA-4503), thyrotropin releasing hormone agonist (e.g., JTP-2942, L-prolinamide and posatirelin), prolyl endopeptidase inhibitor, monosialoganglioside GM1, proteolytic enzyme inhibitor (e.g., nafamostat), neutrophil inhibitory factor, platelet activating factor antagonist (e.g., nupafant), monoamine oxidase B inhibitor (e.g., parafluoroselegiline and benzonitrile derivatives), PARS inhibitors, Angiotensin I converting enzyme inhibitor (e.g., perindopril and ramipril), acetylcholine agonist (e.g., pramiracetam), protein systhesis antagonist (e.g., procysteine), phosphodiesterase inhibitor (e.g., propentofylline), opioid kappa receptor agonist (e.g., 10H-phenothiazine-2-carboxamine derivatives), complement factor inhibitor (sCRI fragments), somatomedin-1, carnitine acetyltransferase stimulant (e.g., acetylcarnitine), and the like;

T cell inhibitors such as synthetic leucocyte antigen derived peptides, interleukin-1 receptor antagonist, MG/AnergiX, anti-CD3 monoclonal antibodies, anti-CD23 monoclonal antibodies, anti-CD28 antibodies, anti-CD2 monoclonal antibodies, CD4 antagonists, anti-E selectin antibodies, MHC inhibitors, monogens, mycophenolate mofetil, LRA-1 inhibitors, selectin inhibitors, and the like;

antimigraine agents, such as MK-462, 324C91, Phytomedicine, (S)-fluoxetine, calcium channel antagonists (e.g., nimodipine/Nimotop, flunarizine, dotarizine/FI-6026, iomerizine HCL/KB-2796, CPC-304, and CPC-317), α-dihydroergocryptine, 5-HT1 agonists, (e.g., Sumatriptan/Imitrex, Imigran, GR-85548, 311C, and GR-127607), 5-HT1D agonists, 5-HT1A antagonists, 5-HT1B antagonists (e.g., CP-93129), 5-HT1D antagonists (e.g., 1H-indole-5-ethanesulfonamide derivatvies and 1H-indole-5-methanesulfonamide), 5-HT1D receptor cloned (e.g., 5-HT1D agents), 2-thiophenecarboxamide, 3-piperidinamine, diclofenac potassium, dihydroergotamine (e.g., DHE 45®), ergotamine tartrate, dolasetron mesilate, dotarizine, flupirtine, histamine-H3 receptor agonist, indobufen, 1-azulenesulfonic acid derivatives, cholinesterase inhibitors, (e.g., S-9977), bradykinin antagonists, nitric oxide reductase inhibitors (e.g., BN-52296), nitric oxide receptor antagonists, substance P antagonists (e.g., Capsaicin/Nasocap), endopeptidase inhibitors (e.g., neutral endopeptidase, cloned), piperazine derivatives, neurokinin 1 antagonists, metergoline, dopamine D2 antagonist (e.g., metoclopramide +lysine acetyl), enkephalinase inhibitors (e.g., neutral endopeptidase), 5-HT2 antagonists (e.g., LY-053857), 5-HT3 antagonists (e.g., Dolasetron mesilate/MDL-73147, and 4H-carbazol-4-one derivatives), tenosal, tolfenamic acid, cyclooxygenase inhibitors (e.g., carbasalate/carbaspirin calcium, and tenosal/MR-Y134), alpha adrenoreceptor antagonists (e.g., arotinolol, and dihydroergocryptine), opioid agonists (e.g., flupirtine/D-9998), beta adrenergic antagonists (e.g., propranolol), valproate semisodium, propanolol hydrochloride, isometheptene mucate, dichloralphenazone, and the like;

antiarthritic agents, such as anti-CD4 monoclonal antibodies, phospholipase A1 inhibitor, loteprednol, tobramycin, combinations of loteprednol and tobramycin, salnacedin, amiprilose, anakinra, anergix, anti-B7 antibody, anti-CD3H, anti-gp39, anti-MHC MAbs, antirheumatic peptides, anti-Tac(Fv)-PE40, AP-1 inhibitors, AR-324, purine nucleotide phosphorylase inhibitors (e.g., BCX-5), bindarit, CD2 antagonist (e.g., BTI-322), campath-1H, CD4 antagonist (e.g., CE9.1 and SB-210396), tumor necrosis factor antagonist (e.g., p80 TNFR, rhTNFbp, peptide T, CenTNF, thalidomide, CDP-571 and TBP-1), cobra venom factor, interleukin 1a agonist (e.g., cytogenin), interleukin 2 receptor antagonist (e.g., dacliximab), ICAM 1 antagonist (e.g., enlimomab), interleukin 1 beta converting enzyme inhibitors (e.g., ICE-inhibitors), interferons (e.g., thymocartin), interleukin-10, interleukin-13, interleukin 1 antagonist (e.g., SR-31747 and TJ-114), interleukin-2 antagonist (e.g., sirolimus), phospholipase C inhibitor, neurokinin 1 antagonist (e.g., L-733060), laflunimus, leflunomide, leucotriene antagonists, levamisole, LFA3TIP, macrocyclic lactone, MHC class II inhibitors, mizoribine, mycophenolate mofetil, NfkB inhibitors, oncolysin CD6, peldesine, pidotimod, PKC-RACK inhibitors, PNP inhibitors, reumacon, CD28 antagonist, roquinimex, RWJ-50271, subreum, T7 vector, tacrolimus, VLA antagonist (e.g., TBC-772), transforming growth factor beta agonist, methionine synthase inhibitors (e.g., vitamin B12 antagonist), adenosine A2 receptor agonist (e.g., YT-146), CD5 antagonist (e.g., zolimomab), 5-lipoxygenase inhibitor (e.g., zileuton, tenidap, and ABT-761), cyclooxygenase inhibitor (e.g., tenoxicam, talmetacin, piroxicam, piroxicam cinnamate, oxaprozin, NXTHIO, ML-3000, mofezolac, nabumetone, flurbiprofen, aceclofenac, diclofenac, and dexibuprofen), metalloproteinase inhibitor (e.g., XR-168, TNF convertase inhibitors, GI-155704A, AG-3340 and BB-2983), nitric oxide synthase inhbitors (i.e, ARL-16556), phospholipase A2 inhibitor (e.g., ARL-67974), selectin antagonist (e.g., CAM inhibitors), leucotriene B4 antagonist (e.g., CGS-25019C), collagenase inhibitor (e.g., GR-129574A), cyclooxygenase 2 inhibitor (e.g., meloxicam), thromboxane synthase inhibitor (e.g., curcumin), cysteine protease inhibitor (e.g., GR-373), metalloproteinase inhibitor (D-5410), lipocortins synthesis agonist (e.g., rimexolone, predonisolone 21-farnesylate, HYC-141, and deflazacort), chelating agent (diacerein), elastase inhibitors, DNA directed RNA polymerase inhibitor (e.g., estrogens), oxygen radical formation antagonist (e.g., glucosamine sulfate), thrombin inhibitors (e.g., GS-522), collagen inhibitors (e.g., halofuguinone), hyaluronic acid agonist (e.g., NRD-101, hylan, Dispasan, and Hyalart), nitric oxide antagonists (e.g., hydroxocobalamin), stromelysin inhibitors (e.g., L-758354), prostaglandin E1 agonist (e.g., misoprostol, and misoprostol+diclofenac), dihydrofolate reductase inhibitor (e.g., trimetrexate, and MX-68), opioid antagonist (e.g., nalmefene), corticotropin releasing factor antagonist (e.g., NBI-103, and NBI-104), proteolytic enzyme inhibitor (e.g., protease nexin-1, and NCY-2010), bradykinin antagonist (e.g., tachykinin antagonists, and NPC-17731), growth hormone antagonist (e.g., octreotide), phosphodiesterase IV inhibitor (e.g., PDEIV inhibitors), gelatinase inhibitor (e.g., REGA-3G12), free radical scavengers (e.g., SIDR-1026), prostaglandin synthase inhibitors (e.g., sulfasalazine), phenylbutazone, penicillamine, salsalate, azathioprine, indomethacin, meclofenamate sodium, gold sodium thiomalate, ketoprofen, auranofin, aurothioglucose, tolmetin sodium, and the like;

antigout agents (e.g., colchicine, allopurinol, and the like);

anticoagulants (e.g., heparin, heparin sodium, warfarin sodium, and the like);

thrombolytic agents (e.g., urokinase, streptokinase, altoplase, and the like);

antifibrinolytic agents (e.g., aminocaproic acid);

hemorheologic agents (e.g., pentoxifylline);

antiplatelet agents (e.g., aspirin, empirin, ascriptin, and the like);

anticonvulsants (e.g., valproic acid, divalproate sodium, phenytoin, phenytoin sodium, clonazepam, primidone, phenobarbitol, phenobarbitol sodium, carbamazepine, amobarbital sodium, methsuximide, metharbital, mephobarbital, mephenytoin, phensuximide, paramethadione, ethotoin, phenacemide, secobarbitol sodium, clorazepate dipotassium, trimethadione, and the like);

agents useful for calcium regulation (e.g., calcitonin, parathyroid hormone, and the like);

antibacterial agents (e.g., amikacin sulfate, aztreonam, chloramphenicol, chloramphenicol palmitate, chloramphenicol sodium succinate, ciprofloxacin hydrochloride, clindamycin hydrochloride, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, colistin sulfate, and the like);

antifungal agents (e.g., griseofulvin, keloconazole, and the like);

antiviral agents (e.g., interferon gamma, zidovudine, amantadine hydrochloride, ribavirin, acyclovir, and the like);

antimicrobials (e.g., cephalosporins (e.g., cefazolin sodium, cephradine, cefaclor, cephapirin sodium, ceftizoxime sodium, cefoperazone sodium, cefotetan disodium, cefutoxime azotil, cefotaxime sodium, cefadroxil monohydrate, ceftazidime, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, cefuroxime sodium, and the like), penicillins (e.g., ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G potassium, penicillin G procaine, methicillin sodium, nafcillin sodium, and the like), erythromycins (e.g., erythromycin ethylsuccinate, erythromycin, erythromycin estolate, erythromycin lactobionate, erythromycin siearate, erythromycin ethylsuccinate, and the like), tetracyclines (e.g., tetracycline hydrochloride, doxycycline hyclate, minocycline hydrochloride, and the like), and the like);

antioxidants (e.g., N-acetylcsysteine, Vitamin A, Vitamin C, Vitamin E, β-carotene, EUK-8, flavonoids, glutathione, αlipoic acid, melatonin, retinols, and the like);

anti-infectives (e.g., miconazole, vidarabine, inosine, pranobex, vidarabine, inosine prabonex, cefpimizole sodium), fradiomycin, and the like);

bronchodialators (e.g., sympathomimetics (e.g., epinephrine hydrochloride, metaproterenol sulfate, terbutaline sulfate, isoetharine, isoetharine mesylate, isoetharine hydrochloride, albuterol sulfate, albuterol, bitolterol, mesylate isoproterenol hydrochloride, terbutaline sulfate, epinephrine bitartrate, metaproterenol sulfate, epinephrine, epinephrine bitartrate), anticholinergic agents (e.g., ipratropium bromide), xanthines (e.g., aminophylline, dyphylline, metaproterenol sulfate, aminophylline), mast cell stabilizers (e.g., cromolyn sodium), inhalant corticosteroids (e.g., flurisolidebeclomethasone dipropionate, beclomethasone dipropionate monohydrate), salbutamol, beclomethasone dipropionate (BDP), ipratropium bromide, budesonide, ketotifen, salmeterol, xinafoate, terbutaline sulfate, triamcinolone, theophylline, nedocromil sodium, metaproterenol sulfate, albuterol, flunisolide, and the like);

hormones (e.g., androgens (e.g., danazol, testosterone cypionate, fluoxymesterone, ethyltostosterone, testosterone enanihate, methyltestosterone, fluoxymesterone, testosterone cypionate), estrogens (e.g., estradiol, estropipate, conjugated estrogens), progestins (e.g., methoxyprogesterone acetate, norethindrone acetate), corticosteroids (e.g., triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate methylprednisolone sodium succinate, hydrocortisone sodium succinate, methylprednisolone sodium succinate, triamcinolone hexacatonide, hydrocortisone, hydrocortisone cypionate, prednisolone, fluorocortisone acetate, paramethasone acetate, prednisolone tebulate, prednisolone acetate, prednisolone sodium phosphate, hydrocortisone sodium succinate, and the like), thyroid hormones (e.g., levothyroxine sodium) and the like), and the like;

hypoglycemic agents (e.g., human insulin, purified beef insulin, purified pork insulin, glyburide, chlorpropamide, glipizide, tolbutamide, tolazamide, and the like);

hypolipidemic agents (e.g., clofibrate, dextrothyroxine sodium, probucol, lovastatin, niacin, and the like);

proteins (e.g., DNase, alginase, superoxide dismutase, lipase, and the like);

nucleic acids (e.g., sense or anti-sense nucleic acids encoding any therapeutically active protein, including the proteins described herein, and the like);

agents useful for erythropoiesis stimulation (e.g., erythropoietin);

antiulcer/antireflux agents (e.g., famotidine, cimetidine, ranitidine hydrochloride, and the like);

antinauseants/antiemetics (e.g., meclizine hydrochloride, nabilone, prochlorperazine, dimenhydrinate, promethazine hydrochloride, thiethylperazine, scopolamine, and the like);

septic shock agents, such as angiogenesis inhibitors (OLX-514), bradykinin antagonists (e.g., CP-0502, and NPC-1773 1), complement factor inhibitors (e.g., C3 convertase inhibitor), C5a release inhibitors (e.g., CAB-2.1), dopamine agonists (e.g., dopexamine), elastase inhibitors (e.g., ONO-5046), E selectin antagonists (e.g., CY-1787), farnesyltransferase inhibitors (RBE limonene), immunostimulants (e.g., CGP-19835A, lipid A vaccine, edobacomab, nebacumab, StaphGAM, and diabodies), immunosuppressants (e.g., CytoTAB, and transcyclopentanyl purine analogues), interleukin 1 antagonists (e.g., interleukin 1 receptors), interleukin 1 receptor antagonists (e.g., anakinra), interleukin 1b antagonists (e.g., interleukin-1β), interleukin 1 beta converting enzyme inhibitors (e.g., ICE-inhibitors), interleukin 8 antagonists (e.g., IL-8 receptor), interleukin 13 agonists (e.g., intereleukin-13), ITF-1697, lipase clearing factor inhibitors (e.g., SC-59735), membrane permeability enhancers (e.g., Bactericidal Permeability Increasing protein/BPI), nitric oxide antagonists (e.g., hydroxocobalamin), nitric oxide synthase inhibitors (e.g., L-NMMA, and α-methyl-N-delta-iminoethyl-ornithine), P2 receptor stimulants (e.g., ATP analogues), phosphatidic acid synthesis antagonists (e.g., lisofylline), phospholipase A2 inhibitors (e.g., S-448, acylpyrrole-alkanoic acid derivatives, and indoleacetic acid derivatives), platelet activating factor antagonists (e.g., ABT-299, TCV-309, SM-12502, (2RS, 4R)-3-(2-(3-pyridinyl)-thiazolidin-4-oyl)indoles, UR-12670, and E-5880), prostacyclin agonists (e.g., taprostene), prostaglandin E1 agonists (e.g., TLC C-53), protein kinase inhibitors (e.g., SB-203580), protein kinase C inhibitors, protein synthesis antagonists (e.g., procysteine), proteolytic enzyme inhibitors (e.g., nafamostat), SDZ-PMX-622, selectin antagonists (e.g., sulfated glycolipid cell adhesion inhibitors), thrombin inhibitors (e.g., GS-522), TNF receptor-Ig, tumor necrosis factor antagonists (e.g., anti-TNF MAbs, MAK-195F, TBP-I, Yeda, rhTNFbp, and CDP-571), tumor necrosis factor alpha antagonists (e.g., E-5531), and the like;

multiple sclerosis agents, such as 4-aminopyridine, 15±deoxyspergualin, ACTH, amantadine, antibody adjuvants (e.g., poly-ICLC, and poly-IC+poly-L-lysine+carboxymethylcellulose), anti-cytokine MAb (CDP-835), anti-inflammatory (e.g., CY-1787, and CY-1503), anti-selectin MAb (e.g., CY-1787), anti-TCR MAb (e.g., NBI- 114, NBI-115, and NBI-116), bacloten, bethanechol chloride, carbamazepine, carbohydrate drugs (e.g., CY-1503), clonazepam, CNS and immune system function modulators (e.g., NBI-106, and NBI-107), cyclophosphamide, cyclosporine A, cytokines (e.g., IFN-α, alfaferone, IFN-β1b, betaseron, TGF-β2, PEG-TGF-β2, betakine, IFN-β/Rebif, frone, interferon-β, and IFN-β), CD4+T cell inhibitors (e.g., AnergiX), CD28 antagonists (e.g., B7-1, B7-2, and CD28), directcytotoxicity therapies (e.g., benzoporphyrin derivative (BPD)), FK-506, growth factors (e.g., glial growth factor, GGF, nerve growth factors, TGF-β2, PEG-TGF-β2, and betakine), humanized MAb (e.g., anti-IFN-γMAb, smart anti-IFN-γMAb, anti-Tac antibody, and smart anti-Tac antibody), humanized anti-CD4 MAb (e.g., anti-CD4 MAb, centara), hydrolase stimulants (e.g., castanospermine), IFN-α, IFN-γ antagonist (e.g., anti-IFN-γMAb, and smart anti-IFN-γMAb), IL-2 antagonists (e.g., tacrolimus, FK-506, FR-900506, Fujimycin, Prograf, IL-2 fusion toxin, and $DAB_{389}IL$-2), IL-4 antagonists (e.g., IL-4 fusion toxin, and $DAB_{389}IL$-4), immune-mediated neuronal damage inhibitors (e.g., NBI-114, NBI-115, and NBI-116), immunoglobins, immunostimulants (e.g., poly-ICLC, edelfosine, ALP, ET-18-OCH3, ET-18-OME, NSC-24, and poly-IC+poly-L-lysine+carboxymethyl-cellulose), immunosuppressants (e.g., azathioprine, AI-100 animal protein, rDNA human protein AI-101, peptide, AI-102, castanospermine, tacrolimus, FK-506, FR-900506, Fujimycin, Prograf, anti-leukointegrin MAb, Hu23F2G, primatized anti-CD4 antibody, CE9.1, Galaptin 14-1, GL14-1, Lectin-1, recombinant IML-1, linomide, roquinimex, LS-2616, transcyclo-pentanyl purine analogs, MS-6044, spanidin, 15-deoxyspergualin, deoxyspurgiline, gusperimus HCL, NSC-356894, NKT-01, TCR, CD3/Ti, cyclosporine, OL-27-400, SandImmune, Human IL-10, monogens, anti-TCR MAbs, TCAR MAbs, Monogen TM19, Monogen TM27, Monogen TM29, Monogen TM31, peptigen TP12, anti-CD4 MAb, cantara, immunophilins, VX-10367, VX-10393, VX-10428, synthetic basic copolymer of amino acids, copolymer-1, COP-1, T lymphocyte immunofusion (TIF) protein, and cyclophosphamide), integrin antagonists (e.g., anti-integrin (cell adhesion molecule α4β1 integrin) MAbs, AN-100225, and AN-100226), interferon agonists (e.g., poly-ICLC, and poly-IC+poly-L-lysine+carboxymethyl-cellulose), interferon-β-1b, isoprinosine, IV methylprednisolone, macrolides (e.g., tacrolimus, FK-506, FR-900506, Fujimycin, and Prograf), MAO B inhibitors (e.g., selegiline, and Parkinyl), methotrexate, mitoxantrone, muscle relaxants (e.g., RGH-5002), muscarinic antagonists (e.g., RGH-5002), neurosteroids (e.g., NBI-106, and NBI-107), octapeptides (e.g., peptide T), oxybutinin chloride, oxygen free radical antagonists (e.g., tetrandrine, biobenzyl-isoquinoline alkaloid), peptide agonists (e.g., peptide T), phenoxybenzamine, phospholipase C inhibitors (e.g., edelfosine, ALP, ET-18-OCH3, ET-18-OME, NSC-24), photodynamic therapies (e.g., benzoporphyrin derivative (BPD)), plasmapheresis, platelet activating factor antagonists (e.g., ginkgolide B, and BN-52021), potassium channel agonists (e.g., aminodiaquine, and EL-970), propranolol, prostaglandin synthase inhibitors (e.g., sulfasalazine, salazosulfa-pyridine, PJ-306, SI-88, azulfidine, salazopyrin), protease antagonists (e.g., ginkgolide B, and BN-52021), recombinant soluble IL-1 receptors, spergualin analogs (e.g., spanidin, 15-deoxyspergualin, deoxyspurgiline, gusperimus HCl, NSC-356894, NKT-01), TCR peptide decoys (e.g., NBI-114, NBI-115, and NBI-116), TCR peptidomimetic decoys (e.g., NBI-114, NBI-115, and NBI-116), TCR peptide vaccines (e.g., AI-208 (Vβ6.2/6.5 phenotype)), selectin antagonists (e.g., lectin-1, and recombinant IML-1), soluble TNF receptor I, TCARs (e.g., TCR, CD3/Ti, and peptigen TP12), TNF antagonists (e.g., thalidomide, and TNF inhibitors), tricyclic antidepressants, and the like;

organ transplantation agents, such as anti-CD25 MAbs, anti-Tac antibodies, anti-TNF MAb (e.g., CDP571), apoptosin, azathioprines (e.g., imuran), BCX-34, CA3, CD28, complement inhibiting factors (e.g., CD59), CTLA4Ig, cyclosporines (e.g., CsA), FK-506/rapamycin binding proteins (FKBP), glucocorticoids, humanized version of OKT3 (e.g., huOKT3-185), mycophenolate mofetil, hydroorotate dehydrogenase inhibitors (e.g., Brequinar), orthoclone OKT3 (e.g., IgG2a anti-T cell murine monoclonal antibody, and muromonab-CD3), rapamycins (e.g., AY-22989), and streptomyces isolates (e.g., FR-900520, and FR-900523), and the like;

systemic lupus erythematosus (SLE) agents, such as androgen-derived steriods (e.g., Org-4094), anti-CD4 humanized antibodies, anti-DNA/V-88, anti-idiotypic murine MAb (e.g., anti-idiotypic antibody to 3E10/MAb1C7), CD2 antagonists (e.g., CD2), complement inhibitors (e.g., recombinant MCP-based complement inhibitors), cyclosporines (e.g., Sandimmune, cyclosporine analog, OG-37325, cyclosporin-G, and NVal-CyA), cytokines (e.g., IL-4 fusion toxin), cytokine receptor antagonists (e.g., immunomodulatory cytokines), E-selectin antagonists (e.g., anti-ELAM, and CY-1787), FK506/tacrolimus (e.g., Prograf), hypercalcemic agents (e.g., KH-1060), IFN-y antagonists (e.g., anti-IFN-γ MAb, and smart anti-IFN-γ MAb), IL-1β converting enzyme inhibitors (ICE), IL-2 produced by *E. coli* (e.g., celmoleukin, IL-2, TGP-3, and Celeuk), immunoglobulins (e.g., anti-ELAM, CY-1788, and humanized CY-1787), immunostimulants (e.g., thymotrinan, RGH-0205, and TP3), immunosuppressants (e.g., Rapamycin, AY-22989, NSC-226080, NSC-606698, anti-CD4, T-cell inhibitor, anti-tac MAb, smart anti-tac MAb, Migis (membrane immunoglobulin-isotope specific) antibodies, SM-8849, immunophilins, VX-10367, VX-10393, VX-10428, mycophenolate mofetil, ME-MPA, RS-61444, cyclosporine, OL-27-400, Sandimmune, IL-4 fusion toxin, trypanosomal inhibitory factor (TIF), T-cell receptor, CD3/Ti, Org-4094, anti-TBM, CP 17193, Leflunomide/A-77-1726, ELAM-1, AnergiX, Spanidin, 15-deoxyspergualin, deoxyspurgiline, gusperimus hydrochloride, NSC-356894, NKT-01, Roquinimex, LS-2616, linomide, LJP-394, and CD-59 antigen), immunotoxins (e.g., Zolimomab aritox, xmmly-h65-rta, xomazyme-lym/CD5-Plus, OrthoZyme-CD5+, XomaZyme-H65-rta, Xomazyme-CD5 Plus), intravenous immunoglobulins (e.g., IVIG), integrin antagonists (e.g., integrin blockers), Migis™ antibodies, monoclonal antibody therapeutics, murine MAb (e.g., anti-SLE vaccine, and MAb 3E10), primatized anti-CD4 antibodies (e.g., CE9.1), protease inhibitors (e.g., matrix metalloprotease (MMP) inhibitors, and stromelysin), protein synthesis antagonists (e.g., anti-CD6-bR, anti-T12-bR, and oncolysin CD6), purine nucleoside phosphorylase inhibitors (e.g., BCX-25, and BCX-14), selectin antagonists (e.g., CY1503, and Cylexin), spergualin analogues (e.g., Spanidin, 15-deoxyspergualin, deoxyspurgiline, gusperimus hydrochloride, NSC-356894, and NKT-01), T cell inhibitors (e.g., AnergiX), tumor necrosis factor (TNF) antagonists, and the like;

Alzheimer's disease agents, such as ACh release enhancers (e.g., T-588 (benzothiophene derivative)), acetylcholine release stimulants (e.g., DUP-996 and analogues), AMPA agonists (e.g., AMAlex, and Isoxazole compound series), AMPA GluR agonist (e.g., IDRA-21 [7-chloro-3-methyl-3,4-dihydro-2H-1,2,4-benzothiadizinine]), AMPA GluR antagonists (e.g., S-18986, and related quinolone derivatives), anticholinesterases (e.g., E-2020), Ca-antagonists (e.g., NS-649, spider venom-derived ICM peptides and analogues, and substituted 2-aminoindanes compound series), combined anticholinesterase and muscarinic AChR antagonists (e.g., PD 142676), K-channel blockers (e.g., Trans-R-4-(4-methoxyphenyl-methyl) cyclohexylanine and analogues, and margatoxin-based functional and/or structural analogues), MI muscarinic receptor agonists (e.g., Xanomeline), NMDA antagonists (e.g., certain indole derivatives, and $(R-(R^1,S^1))-\alpha-(4-$ hydroxyphenyl)-beta-methyl-4-(phenylmenthyl)-1-piperidinepropanol and analogues), nicotinic AChR agonists (e.g., ABT-418 [isoxazole, 3-meth-5-(1-meth-2-pyrrolidinyl)]), and the like;

antiparkinson agents (e.g., ethosuximide, and the like);

psoriasis agents, such as 5-LO inhibitors (e.g., Wy-50295, Wy-49232, Lonapalene, RS-43179, MK-886, L-663536, ETH-615, DUP-654, Zileuton, epocarbazolin-A, and A-64077), 5-LO/CO inhibitors (e.g., BF-397, Tenidap, CP-309, and CP-66248), angiogenesis inhibitors (e.g., platelet factor 4), anticancer antibiotic (e.g., AGM-1470, and TNP-470), anti-inflammatory cytochrome P450 oxidoreductase inhibitors (e.g., DuP-630, and DuP-983), antiproliferative compounds (e.g., Zyn-Linker), arachidonic acid analogues (e.g., CD581, and CD554), arachidonic acid antagonists (e.g., Lonopalene, RS-43179, triamcinolone acetonide with penetration enhancer Azone, betamethasone dipropionate steroid wipe, G-202, Halobetasol propionate, ultravate, Halometasone, C-48401-Ba, and Sicorten), beta-glucan receptor antagonists, betamethasone steroid wipes, calcium metabolic moderators (e.g., Tacalcitol, Bonealfa, TV-02 ointment, Ro-23-6474, KH-1060, Calcipotriol, BMS-181161, BMY-30434, Dovonex, and Divonex), CD4 binding inhibitors (e.g., PIC 060), cell adhesion compounds (e.g., CY-726, VCAM-1, ELAM-1, and ICAM), cell adhesion inhibitors (e.g., selectin inhibitor, GM-1930), cellular aging inhibitors (e.g., Factor X), corticosteroids (e.g., Halobetasol propionate, ultravate, Halometasone, C-48401-Ba, and Sicorten), cyclosporin analogues (e.g., IMM-125), dihydrofolate reductase inhibitors (e.g., G-301, dichlorobenzoprim, methotrexate, and methotrexate in microsponge delivery system), E-selectin inhibitors (e.g., ISIS 4730), endogenous active form of vitamin $D_3$ (e.g., Calcitriol, and Du-026325), fibroblast growth factor antagonists (e.g., Saporin mitotoxin, and Steno-Stat), fumagillin analogues (e.g., AGM-1470, and TNP-470), G-proteins and signal transduction compounds (e.g., CPC-A), gel formulations for acne (e.g., nicotinamide, N-547, and Papulex), growth hormone antagonists (e.g., Octreotide, Sandostatin, Lanreotide, angiopeptin, BIM-23014, and Somatuline), humanized antibodies (e.g., anti-CD4 antibody), hydroorotate dehydrogenase inhibitors (e.g., Brequinar sodium, bipenquinate, and DuP-785), ICAM-1 inhibitors (e.g., ISIS 939), IL-1 and other cytokine inhibitors (e.g., Septanil), IL-1 converting ezyme inhibitors, IL-1 receptor antagonists (e.g., Antril), IL-2 antagonists (e.g., Tacrolimus, Prograf, and FK-506), IL-2 receptor-targeted fusion toxins (DAB389IL-2), IL-8 receptors, immunostimulants (e.g., Thymopentin, and Timunox), immunosuppressants (e.g., XomaZyme-CD5 Plus, cyclosporine, Sandimmune, SR-31747, anti-CD 11, 18 MAb, Tacrolimus, Prograf, FK-506, and FK-507), immunosuppressive agents targeting FK506 (e.g., immunophilins, VX-10367, and VX-10428), immunotoxins MAb directed against CD antigen (e.g., XomaZyme-CD5 Plus), leukotriene antagonists (e.g., Sch-40120, Wy-50295, and Wy49232), leukotriene B4 antagonists (e.g., SC-41930, SC-50605, SC-48928, ONO-4057, LB-457, LY-255283, LY-177455, LY-223982, LY-223980, and LY-255253), leukotriene synthesis inhibitors (MK-886, and L-663536), lipase clearing factor inhibitors (e.g., 1-docosanol, and lidakol), lipid encapsulated reducing agent (e.g., Dithranol), liposomal gel (e.g., Dithranol), LO inhibitors (e.g., CD581, CD554, Masoprocol, and Actinex), lithium succinate ointments (e.g., lithium salts, and Efalith), LO/CO inhibitors (e.g., P-8892, P-8977, CHX-108, and FPL-62064), membrane integrity agonists (e.g., lithium salts, and Efalith), microtubule inhibitors (e.g., Posophyliotoxin-containing compound, and Psorex), octapeptide somatostatin analogues (e.g., Lanreotide, angiopeptin, BIM-23014, and Somatuline), oligonucleotides (e.g., ISIS 4730, ISIS 3801, ISIS 1939, and IL-1 inhibitors), peptide agonists (e.g., octapeptide, and peptide T), PKC inhibitors, phospholipase A2 compounds, pospholipase D compounds, photodynamic anticancer agents (e.g., 5-aminolevulinic acid, and 5-ALA), photodynamic therapies (e.g., benzoporphyrin derivative, synthetic chlorins, synthetic porphyrins, and EF-9), photosensitizer (e.g., Porfirmer sodium), PKC inhibitors (e.g., Safingol, and Kynac), platelet activating factor antagonists (e.g., TCV-309), platelet aggregation inhibitors (e.g., CPC-A), prodrug NSAIDs (e.g., G-201), prostaglandin agonist (e.g., eicosapentaenoic acid +gamma-linolenic acid combination, and Efamol Marine), protein inhibitors (e.g., SPC-103600, and SPC-101210), protein kinase C (PKC) inhibitors (e.g., Ro-31-7549, Ro-31-8161, and Ro-31-8220), protein synthesis antagonists (e.g., Calcitriol, Du-026325, LG-1069, LG-1064, AGN-190168, Namirotene, and CBS-211A), purine nucleoside phosphorylase inhibitors (e.g., BCX-34), radical formation agonists (e.g., benzoporphyrin derivative), recombinant antileukoproteinases (e.g., ALP-242), retinoids (e.g., BMY-30123, LG-1069, and LG-1064), retinoid derivatives (e.g., AGN-190168), rapamycin binding proteins (FKBP) (e.g., immunophilins, VX-10367, and VX-10428), second generation monoaromatic retinoids (e.g., Acitretin, and Neotigason), soluble IL-1, IL-4 and IL-7 receptors, somatostatin and somatostatin analogues (e.g., Octreotide, and Sandostatin), steroids, (e.g., AGN-191743), streptomyces anulatus isolates (e.g., epocarbazolin-A), superoxide dismutase (e.g., EC-SOD-B), thymidylate synthase inhibitors (e.g., AG-85, MPI-5002, 5-FU in biodegradable gel-like matrix, 5-FU and epinephrine in biodegradable gel-like matrix, and AccuSite), topical formulations (e.g., P-0751, and P-0802), transglutaminase inhibitors, tyrphostin EGF receptor kinase blockers (e.g., AG-18, and AG-555), VCAM-1 inhibitors (e.g., ISIS 3801), vitamin D analogues (e.g., Ro-23-6474, KH-1060, Calcipotriol, BMS-181161, BMY-30434, Dovonex, and Divonex), vitamin $D_3$ analogues (e.g., Tacalcitol, 20 Bonealfa, TV-02 ointment), and vitamin $D_3$ derivatives (e.g., 1,2-diOH-vitamin $D_3$), and the like;

diabetes agents, such as ACE inhibitors (e.g., captopril), amylin, amylin agonists and antagonists (e.g., Normylin™, AC137, GC747, AC253, and AC625), autoimmune compounds (e.g., AI-401), capsaicins (e.g., Zostrix-HP), cell regulators (e.g., protein kinase C inhibitors, and Balanol), domperidones (e.g., Motilium®), fluvastatins (e.g., Lescol), FOX 988, fusion toxins (e.g., $DAB_{389}IL-2$, and $DAB_{486}IL-2$), gene therapies (e.g., Transkaryotic Therapies), glucagons (e.g., recombinant yeast glucagon), IL-10 compounds, iloprost, immunosuppressives (e.g., tacrolimus, Prograf, and FK-506), proinsulin, insulin and insulin analogs (e.g., AI-401, Nu-Insulin compounds, Humulin, Iletin, Humalog™ LYs-Pro, and Amaryl), insulin-like growth factors (e.g., Chiron/Ciba-Geigy compounds, Fujisawa compounds, and Genetech compounds), insulinotropins (e.g., Pfizer/Scios Nova compounds), nerve growth factors (e.g., Genentech compounds), oral hypoglycemics (e.g., AS-6, glimepiride, Amaryl, CL 316,243, acarbose, miglitol, recombinant yeast glucagon, GlucaGen™, NovoNorm™ glipizide, insulinotropin, and CI-991/CS-045), platelet-derived growth factors (e.g., Zymo Genetics/Novo Nordisk compounds), sulfonylureas (e.g., tolbutamide, acetohexamide, tolazamide, and chlorpropramide), T cell approaches (e.g., anergize, AnergiX™ Procept compounds, and T cell Sciences compounds), and tolrestats (e.g., Alredase®, and ARI-509), activin, somatostatin, and the like;

stroke agents, such as 5-HT antagonists (e.g., Piperazine derivative), 5-HT reuptake inhibitors (e.g., Milnacipran, and Dalcipran), 5-HT 1A agonists (e.g., SR-57746A, and SR-57746), 5-HT 3 agonists (e.g., SR-57227), 5-HT 4 antagonists, 5-lipoxygenase inhibitors (e.g., low MW dual 5-lipoxygenase and PAF inhibitor CMI-392), ACh agonists (e.g., Pramiracetam, Choline-L- alfoscerate, L-alpha-glycerylphosphoryl-choline, and Delecit), adenosine agonists (e.g., GP-1-4683, ARA-100, and arasine analogs), adenosine Al receptor agonists (e.g., Azaisotere, 2-chloro-N-[4 (phenylthio)-1-piperidinyl] adenosine, and 2120136), adenosine reuptake inhibitors (e.g., Diphenyloxazole derivatives), adrenergic transmitter re-uptake inhibitors (e.g., Bifemelane, E-0687, MCI-2016, Alnert, and Celeport), aldose reductase inhibitors (e.g., Spiro-3' pyrroline derivatives), alpha antagonists (e.g., Drotaverine acephyllinate, and Depogen), alpha 2 agonists (e.g., SNAP-5083, SNAP-5608, and SNAP-5682), AMPA receptor agonists (e.g., heterocyclic compound SYM-1207, and heterocyclic compound SYM-1252), AMPA receptor antagonists (e.g., LY-293558, and LY-215490), Ancrod/Arvin, aspirin, benzothiazoles (e.g., Lubeluzole, and R87926), benzodiazepine receptor antagonists (e.g., 3-oxadiazolyl-1,6-naph-thyridine derivatives, Tetracyclic imidazodiazepineseries imidazenil, FID-02-023, and Ro-23-1412), blood substitutes, bradykinin antagonists (e.g., CP-0127, Bradycor, and Septicor), C5a release inhibitors (e.g., protein derivative CMI-46000), calcium antagonists (e.g., Lemildipine, NB-818, NPK-1886, Trimetazidine derivative, Iomerizine KP-2796, Diltiazem analog clentiazem maleate, and TA-3090), calcium channel antagonists (e.g., nitrendipine-like compound diperdipine, YS-201, U-92032, Diltiazem derivative, 1058, SM-6586, KP-840, F-0401, D-31-D, Tetrahydronaphthalene derivatives, fasudil, AT-877, H-7, HA-1044, HA-1077, Eril, darodipine, dazodipine, PY-108-068, Plimo, Dihydropy-ridine, AE 0047, GJ-0956, Lacidipine, GR-43659, GR-43659X, GX-1048, S-312-d, S-312, S-830312, Nilvadipine, and FK-235), calpain inhibitors (e.g., AK-275, and CX-275), carnitine palmitoyl-transferase inhibitors, carvedilol, cerebral calcium antagonist vasodilators (e.g., Nimodipine, and Nimotop), cholinesterase inhibitors (e.g., indole and indazole derivatives, and Tacrine analog), complement factor inhibitors (e.g., TK9C, protein derivative TP16, compinact A, compinact C, Factor D inhibitors, and soluble, recombinant MCP-based complement inhibitors), complement inhibitors (e.g., sCRI/BRL-55730, and YM-203), coronary vasodilators (e.g., Nicorandil, RP-46417, SG-75, and Adancor), CPC-111, cytidyl diphosphocholine/citicholines, cytokines (e.g., NBI-117), Dexanabiol, dopamine agonists, EAA receptors, endothelin antagonists (e.g., SB 209670), endothelin receptor antagonists, excitatory amino acid agonists (e.g., acylated polyamine analogs, and N-(4-hydroxyphenylpropanonyl)-spermine analog), excitatory amino acid antagonists (e.g., Tryptophan, 4,6-disubstituted stroke & kynurenine derivatives, NPC-17742, CPC-701, and CPC-702), glutamate antagonists (e.g., Kainate quisqualate NNC-07-9202, NPC-17742, small molecule CNS-1237, NS-257, NS-072, BW-619C, CGS 19755, Riluzole, PK-26124, and RP 54274), glutamate receptor antagonists (e.g., Araxin compounds, Quinoxaline derivative, YM-90K, and YM-900), glycine antagonists, glycine NMDA agonists (e.g., 3-hydroxy-2,5-dioxo-1H-benz[b]azepines), glycine NMDA associated antagonists (e.g., 5,6-dihydro-1H-pyrrolo [1,2,3-de]quinoxaline-2,3-diones, Strychnine-insensitive glycine binding site of NMDA receptor L-687414, Glystasins, ACEA-2011, ACEA-3031, AC-1021, ACPC, and eliprodil), growth factor antagonists (e.g., non-peptide indolocarbazole neutrophic molecules, and CEP-075), GPIIb/IIIa antagonists (e.g., Peptide C68-22), hemorheological agents (e.g., Drotaverine acephyllinate, and Depogen), heparin, hydroxyl radical formation inhibitors (e.g., homopiperazine derivative K-7259), hypocalcemic agents (e.g., calcitonin peptide, related to hCGRP peptide), hypothermic agents/BMY-20862, ICAM-1 compounds (e.g., Enlimomab), immunosuppressants (e.g., small molecule compounds, and NBI-117), integrin general antagonists (e.g., monoclonal antibody AN-100225, and monoclonal antibody AN-100226), Interleukin-1 antagonists (e.g., cyclic nitrones), iron-dependent lipid peroxidation inhibitors (e.g., 2-(amino-methyl) chromans), lactic acid accumulation/inhibitors (e.g., small molecule CPC-211), Leukotriene B4 antagonists (e.g., Ebselen, DR-3305, PZ-25, PZ-51, RP 60931, and RP 61605), lipid peroxidase inhibitors (e.g., Idebenone, and Avan), low molecular weight small molecules, methyltransferase stimulants (e.g., 4-methyl benzenesulfonate, ademetionine sulfate tosilate, FO-156, and Ceritan), monoamine oxidase B inhibitors (e.g., MD-280040, MD-200243, MD-280080, Lazabemide, and Ro-19–6327), MS-153, MS-424, /$Na^+$/$H^+Na^+/Li^+$ exchange inhibitors (e.g., Pyrazine derivatives), nadroparin (e.g., Fraxiparin), nafronyl/naftidrofuryl (e.g., Praxilene), nerve growth factor agonists (e.g., small molecule compounds, CNTF, BDNF, 2.5S NGF, monosialoganglioside GM1, and Sigen/Sygen), neuronal calcium channel blockers (e.g., CPC-304, and CPC-317), neuronal differentiation compounds (e.g., F-spondin), neuropeptide agonists (e.g., Neurotrophic Peptide Trofexin), neutrophil inhibitory factors (e.g., small molecule compounds), nitric oxide agonists (e.g., hydroxy derivative N-3393, hydroxy derivative N-3398, nicorandil, and Therapicon), nitric oxide antagonists, NMDA antagonists (e.g., Spiroisoindoles/dizocilpine derivatives, Oxindole compound, CP-112116, LY-104658, LY-235959, FR-115427, Sialic acid derivative, N-palmitoyl-Betaethylglycoside neuraminic acid, ND-37, Ro-01-6794, 706, Dextrorphan, Ifenprodil analogue eliprodil, SL-82.0715, Lipophilic molecules, HU-211, Remacemide, 934-423, 12495, 12859, 12942AA, Selfotel, CGS-19755, SDZ-EAA-494, CGP-40116, CGP-37849, CGP-39551, and CGP-43487), NMDA antagonist-partial agonists (e.g., Conantokin G peptide SYM-1010), NMDA channel blockers (e.g., Aptiganel, CERESTAT, and CNS 1102), NMDA receptor antagonists, NMDA receptor subtypes (e.g., Kainate quisqua-late NNC-07-9202), non-competitive NMDA antagonists (e.g., FPL-15896), non-ionic copolymer RheothRx, nootropic/acetylcholine agonists (e.g., Oxiracetam, CT-848, and Neuractiv), norepinephrine inhibitors (e.g., Midalci-pran), N-type calcium channel antagonists (e.g., NS-626, and NS-638), opioid antagonists (e.g., Nalmefene, nalmetrene, JF-1, ORF-11676, Cervene, and Incystene), opioid kappa receptor agonists (e.g., acrylacetamide enadoline, and CI-997), organose-lenims (e.g., Ebselen, DR-3305, PZ-25, PZ-51, RP 60931, and RP 61605), oxygen scavengers (e.g., Tirilazad mesylate, Lazaroids, and Freedox), PA2 inhibitors (e.g., phospholipase A2 inhibitor), PAF antagonists (e.g., nupafant, and BB-2113), partial glycine NMDA agonists (e.g., ACPC), peptide/GPIIb/IIIa antagonists (e.g., Integrelin), peptidic neuron-specific calcium channel antagonists (e.g., SNX-111), phosphodiesterase inhibitors (e.g., Xanthine derivatives, propentofylline, Hoe-285, and Hextol), phospholipase A2 inhibitors (e.g., small organic molecule CEP-217), plasminogen activators (e.g., r-ProUK (recombinant pro-urokinase), platelet-activating factor antagonists (e.g., UK-74505), platelet adhesion inhibitors (e.g., Peptide), platelet aggregation antagonists (e.g., cilostazol, peptide agents, GPHb-IIIA inhibitor, and TP-9201), platelet aggregation inhibitors (e.g., Diaminoalkanioic acid derivatives), potassium channel agonists (e.g., Nicorandil, RP-46417, SG-75, and Adancor), prolyl endopeptidase (PEP) inhibitors (e.g., JTP-4819), protein kinase C inhibitors (e.g., monosialoganglioside derivative Liga-20), proteolytic enzyme inhibitors (e.g., Protease nexin-1, Incyte, PN-1, PN-2, Nafamostat, FUT-175, Duthan, and Futhan), pyrimidine derivatives, Quinolizine derivatives (e.g., KF-17329, and KF-19863), radical formation antagonists (e.g., EPC-K1), recombinant tissue plasminogen activators (e.g., alteplase, and Activase), Schwann cell derived molecules/promoters, sigma antagonists (e.g., Sigma ligand), sigma receptor antagonists (e.g., tetrahyropyridinyl-isoxazolines and isoxazoles PD-144418), sodium/calcium channel modulators (e.g., Lifarizine, and RS-87476), sodium channel antagonists, streptokinase (e.g., Streptase), substituted guanadine (e.g., small molecule CNS-1237), superoxide dismutase stimulants (e.g., PEG conjugated enzyme superoxide dismutase/Dismutec, and PEG-SOD), thrombin inhibitors, (e.g., non-peptide), thromboxane synthase inhibitors (e.g., Linotroban, and HN-11500), thyrotropin-releasing hormone agonists (e.g., TRH agonists, Protirelin analogthymoliberin, and RX-77368,), ticlopidine (e.g., Ticlid), TJ-8007, TRH agonists (e.g., Thyrotropin releasing hormones, and JTP-2942), trilazard, urokinase (e.g., Abbokinase), w-conopeptide (e.g., SNX-111), and warfarin (e.g., Coumadin), and the like;

agents useful for the treatment of carcinomas (e.g., adriamycin, taxol, interleukin-1, interleukin-2 (especially useful for treatment of renal carcinoma), and the like, as well as leuprolide acetate, LHRH analogs (such as nafare-lin acetate), and the like, which are especially useful for the treatment of prostatic carcinoma), agents useful for the treatment of endometriosis (e.g., LHRH analogs), agents useful for the treatment of uterine contraction (e.g., oxytocin), agents useful for the treatment of diuresis (e.g., vasopressin), agents useful for the treatment of cystic fibrosis (e.g., Dnase (i.e., deoxyribonuclease), SLPI, and the like), agents useful for the treatment of neutropenia (e.g., GCSF), agents useful for the treatment of lung cancer (e.g., beta 1-interferon), agents useful for the treatment of respiratory disorders (e.g., superoxide dismutase), agents useful for the treatment of ischemia/reperfusion injury (e.g., selectin inhibitors, Irf1, and the like);

nitric oxide synthase inhibitors (e.g., $N^4$-methyl-L-arginine, aminoguanidine, N-(iminoethyl)-L-ornithine, thiocitrulline and other citrulline derivatives, $N^4$-nitro-L-arginine, $N^4$-nitro-L-arginine methyl ester, $N^4$-amino-L-arginine, and other arginine derivatives, isothiourea and its derivatives, and the like, as well as a variety of other agents, such as acyclovir, alendronate sodium, amlodipine, ampicillin, azelaic acid, azithromycin, beclomethasone, betamethasone, bicalutamide, buspirone, carisoprodol, carvedilol, cefaclor, cefadroxil, cefixime, cefprozil, ceftibuten, cefuroxime axetil, cephalexin, cetirizine hydrochloride, cimetidine, ciprofloxacin, cisapride, clarithromycin, clavulanate, clonazepam, clotrimazole, codeine, conjugated estrogens, cyclobenzaprine, desogestrel, dexrazoxane, diazepam, dicyclomine HCI, digoxin, diltiazem, dirithromycin, doxazosin, doxycycline, enalapril, erythromycin, erythromycin base, erythromycin stearate, estradiol, ethinyl estradiol, ethynodiol diacetate, etodolac, famotidine, fluconazole, fluoxetine, fluvastatin, furosemide, gemfibrozil, glipizide, glyburide, guaifenesin, hydrochlorothiazide, hydrocodone, hydrocortisone, ibuprofen, ibutilide fumarate, indapamide, insulin, ipratropium bromide, ketoconazole, ketoprofen, ketorolac tromethamine, lamivudine, lansoprazole, levonorgestrel, levothyroxine, lisinopril, loracarbef, loratidine, lorazepam, losartan potassium, lovastatin, medroxyprogestrone, methylphenidate, methylprednisolone, metoprolol, metoprolol tartrate, moexipril hydrochloride, mometasone furoate, mupirocin, mycophenolate mofetil, nabumetone, nalmefene hydrochloride, naproxen, neomycin, nifedipine, nisoldipine, nitrofurantoin, nizatidine, norethindrone, norgestrel, nortriptyline, ofloxacin, omeprazole, oxaprozin, oxycodone, paroxetine, penicillin, pentoxifylline, phenylpropanolamine, phenytoin, polymyxin, porfimer sodium, potassium chloride, pravastatin, prednisone, promethazine, propoxyphene, pseudoephedrine, quinapril, ramipril, ranitidine, riluzole, salmeterol, saquinavir mesylate, sertraline, sevoflurane, simvastatin, sucralfate, sulfamethoxasole, sumatriptan, temazepam, terazosin, terconazole, terfenadine, tetracycline, theophylline, timolol, tramadol, tramadol hydrochloride, tretinoin, triamcinolone acetonide, triamterene, trimethoprim, valproic acid, venlafaxine, verapamil, wafarin, zolpidem, and the like.

The free radical scavenging component (e.g., dithiocarbamate disulfide) and the pharmacalogically active agent of invention conjugates can be covalently attached employing a variety of linkages, e.g., ester linkages, disulfide linkages, amide linkages, ether linkages, thioether linkages, imide linkages, sulfate ester linkages, sulfonate ester linkages, phosphate ester linkages, carbonate linkages, O-glycosidic linkages, S-glycosidic linkages, and the like. Such linkages can be accomplished using standard synthetic techniques as are well known by those of skill in the art, either by direct reaction of the starting materials, or by incorporating a suitable functional group or a linker on the starting material, followed by coupling of the reactants.

Invention dithiocarbamate disulfide-containing conjugates are particularly well suited for oral or local administration because they are stable at the pH in the stomach (and have been shown to be stable at pH 1 for up to 24 hours) but release the active monomers under slightly reducing conditions, such as are found in the lower alimentary tract, in skin and in tissue.

Accordingly, there are provided pharmaceutical compositions comprising a pharmaceutically acceptable carrier, a dithiocarbamate disulfide-containing cojugate as described herein, and optionally further including a simple reducing agent, such as L-cysteine or glutathione, and the like, in an amount sufficient to reduce the disulfide bond in the disulfide component of the conjugate.

In accordance with another embodiment of the present invention, there are provided methods for the preparation of protected forms of pharmacologically active agents, said method comprising covalently attaching a suitable free radical scavenger (e.g., dithiocarbamate disulfides) to said pharmacologically active agent. The resulting conjugate provides a latent form of the pharmacologically active agent, releasing the biological activity thereof only when the covalent bond linking the free radical scavenger (e.g., dithiocarbamate disulfides) to said pharmacologically active agent is cleaved (e.g., by an esterase, amidase or other suitable enzyme). Cleavage of the covalent bond linking the dithiocarbamate disulfide to said pharmacologically active agent also releases dithiocarbamate disulfide and/or free dithiocarbamate, which provides effective free radical scavenging activity directly at the site where free radical production is commonly induced as a result of the disease state being treated and/or as a result of the treatment itself.

As readily recognized by those of skill in the art, invention protected forms of pharmacologically active agents can be prepared in a variety of ways. See, for example, Scheme 1, wherein a pharmacologically active compound (1) bearing a carboxylic moiety can be reacted with a diol to produce ester (3), which can then be activated by treatment with an arylsulfonyl chloride to produce compound (5), which can then be coupled with the salt form of a disulfide such as compound (6) to produce invention compound (7).

Scheme 1
General Procedure for the preparation of Conjugate Compounds 7

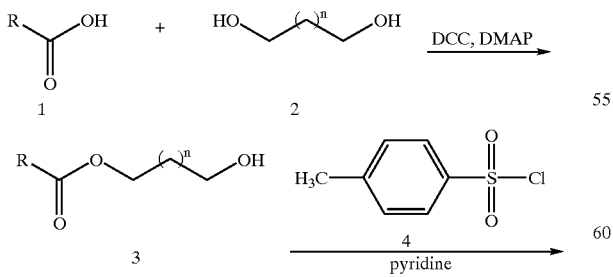

-continued

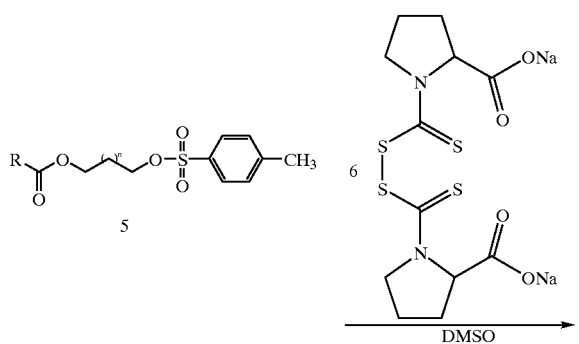

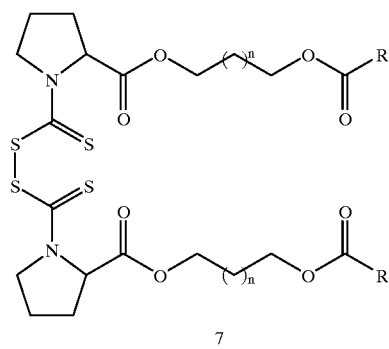

Scheme 2 illustrates application of the general procedure set forth above to the synthesis of L-proline dithiodicarbamate disulfide (PDD) conjugates with naproxen. Thus, reaction of naproxen (8) with propanediol (9) yields intermediate (10), which is then activated to form intermediate (11), which is then converted into the invention conjugate (12).

Scheme 2
Preparation of Conjugate Compound 12

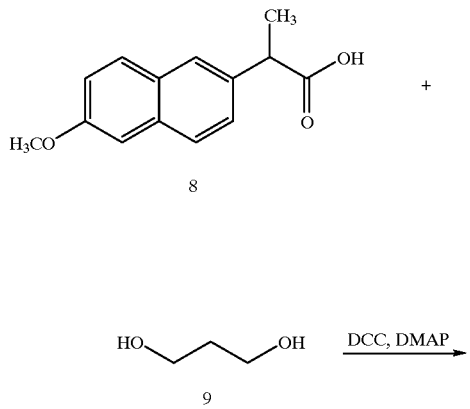

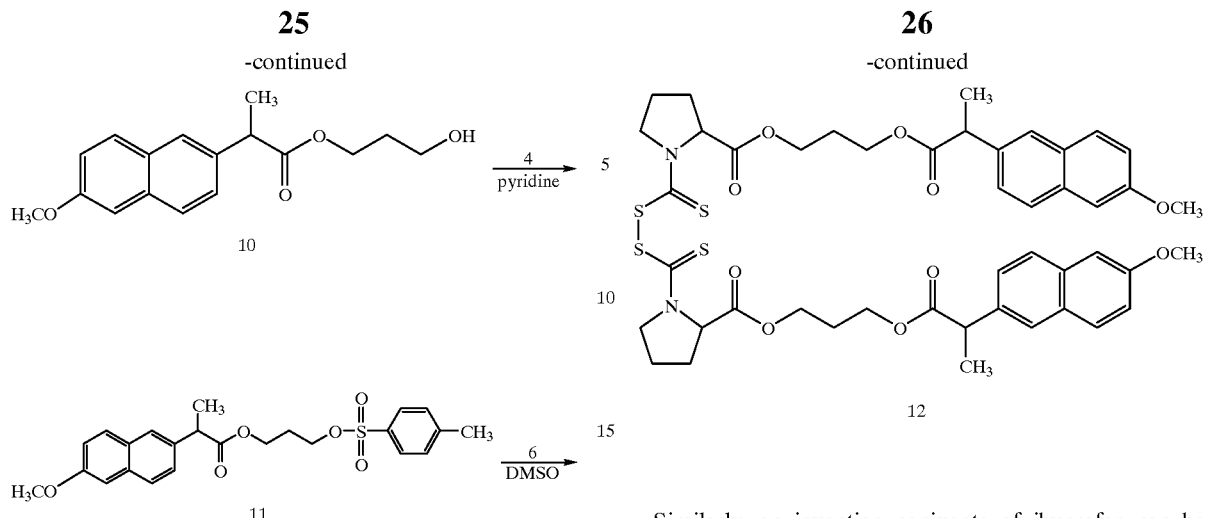
Similarly, an invention conjugate of ibuprofen can be prepared as shown in Scheme 3. Thus, reaction of ibuprofen (13) with propanediol (9) yields intermediate (14), which is then activated to form intermediate (15), which is then converted to invention conjugate (16).
Scheme 3
Preparation of Conjugate Compound 16
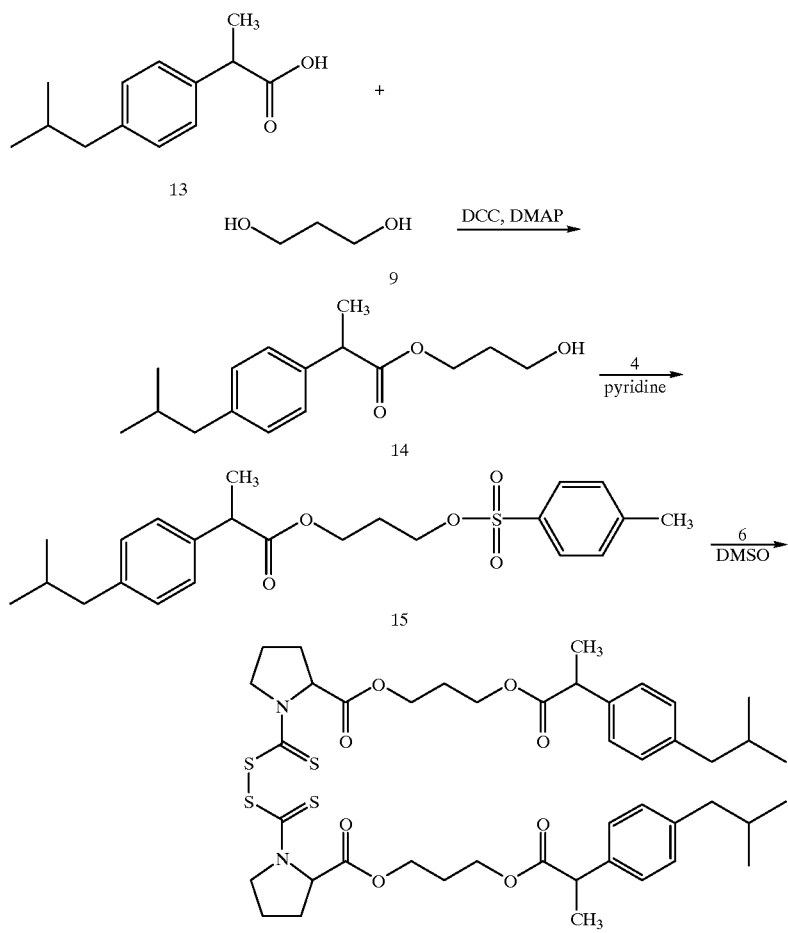

In a similar manner, invention conjugates of ketoprofen can be prepared. See Scheme 4.
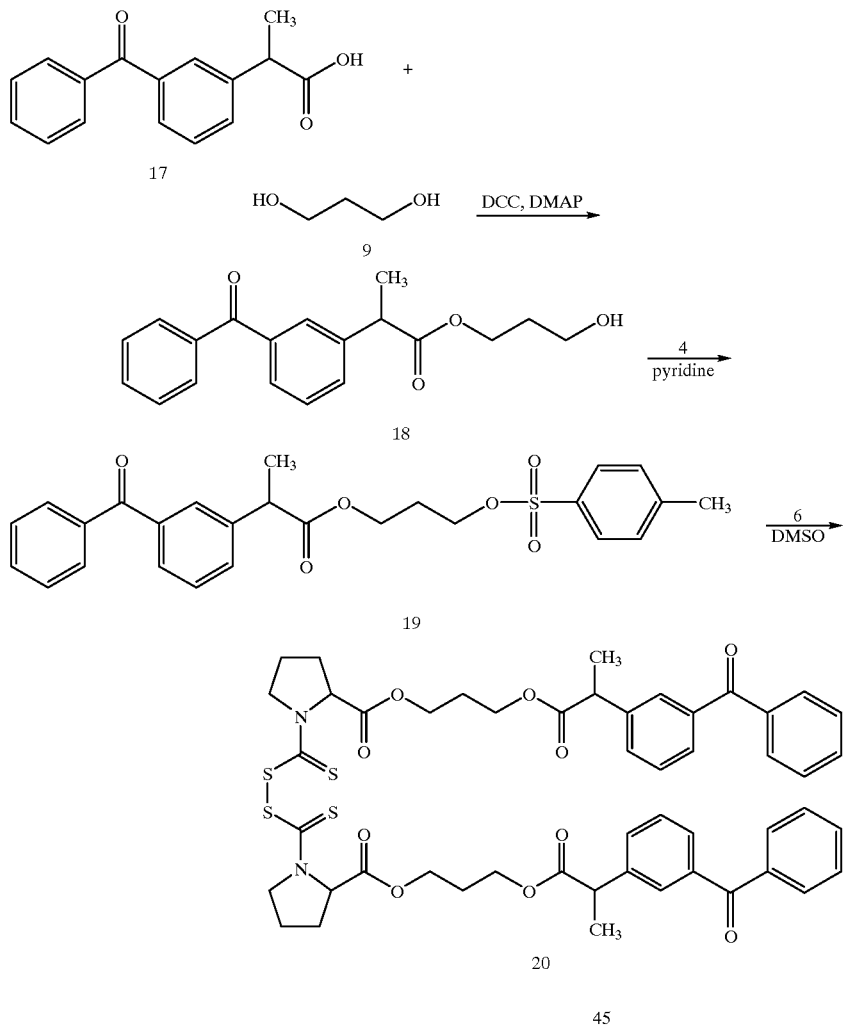
Likewise, invention conjugates of indomethacin can be prepared. See Scheme 5.
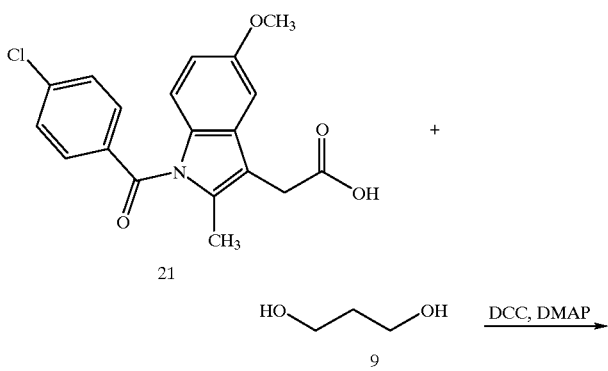

-continued

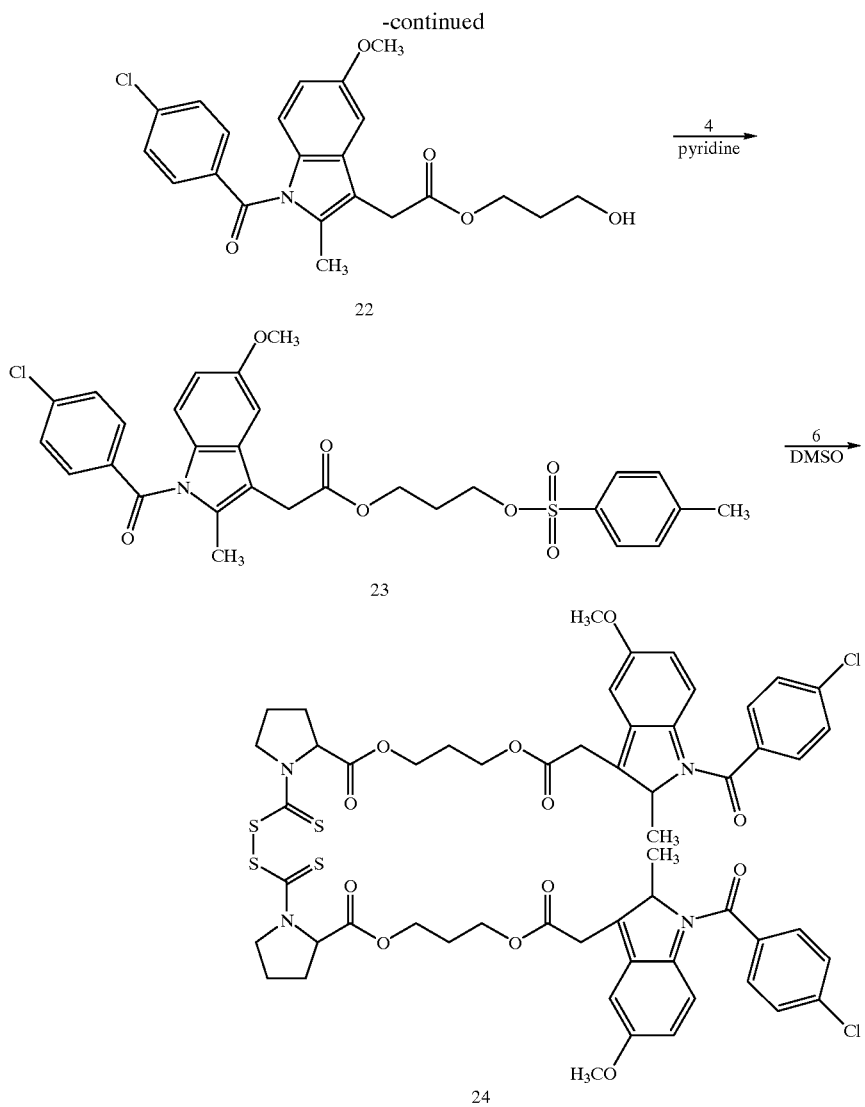

In accordance with yet another embodiment of the present invention, there are provided methods for reducing the side effects induced by administration of pharmacologically active agent(s) to a subject, said method comprising covalently attaching a suitable free radical scavenger (e.g., dithiocarbamate disulfide) to said pharmacologically active agent(s) prior to administration to said subject.

Subjects contemplated for treatment in accordance with the present invention include mammals (such as humans, canines, felines, bovine, ovine, rodents, and the like), fowl (e.g., chicken, turkey, and the like), and so on.

In accordance with still another embodiment of the present invention, there are provided methods for enhancing the effectiveness of pharmacologically active agent(s), said method comprising covalently attaching a suitable free radical scavenger (e.g., a dithiocarbamate disulfide) to said pharmacologically active agent.

In accordance with a still further embodiment of the present invention, there are provided improved methods for the administration of pharmacologically active agent(s) to a subject for the treatment of a pathological condition, the improvement comprising covalently attaching a dithiocarbamate disulfide to said pharmacologically active agent prior to administration of said pharmacologically active agent to said subject.

Those of skill in the art recognize that the free radical scavengers described herein can be delivered in a variety of ways, such as, for example, orally, intravenously, subcutaneously, parenterally, rectally, by inhalation, and the like.

Depending on the mode of delivery employed, the free radical scavengers contemplated for use herein can be delivered in a variety of pharmaceutically acceptable forms. For example, the scavenger can be delivered in the form of a solid, solution, emulsion, dispersion, micelle, liposome, and the like.

Thus, in accordance with still another embodiment of the present invention, there are provided physiologically active composition(s) comprising conjugates prepared from compound(s) having the structure I in a suitable vehicle, rendering said conjugates amenable to oral delivery, transdermal delivery, intravenous delivery, intramuscular delivery, topical delivery, nasal delivery, ocular delivery, and the like.

Pharmaceutical compositions of the present invention can be used in the form of a solid, a solution, an emulsion, a dispersion, a micelle, a liposome, and the like, wherein the resulting composition contains one or more of the conjugates of the present invention, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. The active compound(s) (e.g., one or more pharmacologically active agents, covalently bound to a dithiocarbamate of structure I) is(are) included in the pharmaceutical composition in an amount sufficient to produce the desired effect upon the process or disease condition.

Pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing the active ingredient in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Conjugates contemplated for use in the practice of the present invention may also be administered in the form of suppositories for rectal administration of the drug. These compositions may be prepared by mixing the drug with a suitable non-irritating excipient, such as cocoa butter, synthetic glyceride esters of polyethylene glycols, which are solid at ordinary temperatures, but liquify and/or dissolve in the rectal cavity to release the drug.

Compounds contemplated for use in the practice of the present invention may also be formulated for topical administration, for example, as a skin lotion, suntan lotion, cosmetic lotion, moisturizer, lip balm, eye makeup, face cream, and the like. A typical formulation includes one or more compounds as described herein, in combination with moisturizers, antioxidants, and the like.

Moisturizers contemplated for use in the above-described topical formulations include occlusive moisturizers, such as, for example, hydrocarbon oils and waxes, petroleum jelly, silicone oils, silicone derivatives, vegetable and animal fats, cocoa butter, mineral oil, fatty acids, fatty alcohols, lanolin, phospholipids, and the like; humectants, such as, for example, glycerin, honey, lactic acid, sodium lactate, ceramic, urea, propylene glycol, sorbitol, pyrrolidone carboxylic acid, glycolic acid, gelatin, vitamins, proteins, and the like; hydrophilic matrices, such as, for example, hyaluronic acid, colloidal oatmeal, and the like; essential fatty acids (e.g., Dermasil), elastin, niosomes, and the like.

Antioxidants contemplated for use in the above-described topical formulations include superoxide dismutase, catalase, glutathione peroxidase, glutathione reductase, $\gamma$-tocopherol, $\alpha$-tocopherol, ubiquinol 10, ubiquinone 10, ascorbic acid, uric acid, glutathione, and the like.

Commonly used active ingredients in sunscreen products include para-aminobenzoic acid (PABA), benzophenone, padimate O, cinnamates, homosalate, oxybenzone, octylsalicylates, and the like. Exemplary sunscreen products include Shade SPF15 (available from Schering-Plough Corp., Memphis, Tenn.), Pre-Sun SPF15 cream (available from Westwood-Bristol Myers, Buffalo, N.Y.), Sundown SPF15 (available from Proctor and Gamble, Cincinnati, Ohio), Bullfrog SPF36 (available from Chattem, Inc., Chattanooga, Tenn.), Daylong 16 (available from SpirigAG, CH-Egerkingen, an emulsion gel containing 70% water, ethanol, phospholipids, carbopol, sorbitol, silicone, amphisol, cetyl alcohol, tocopherol, triethanolamine, preservatives, and preparations with white petroleum jelly as vehicle, and the like.

Commonly used active ingredients in skin care products include alpha-hydroxy acids, tocopherol sorbate, ascorbate, glycolic acid, and the like.

Since individual subjects may present a wide variation in severity of symptoms and each drug has its unique therapeutic characteristics, the precise mode of administration and dosage employed for each subject is left to the discretion of the practitioner.

In general, the dosage of conjugate of the invention employed as described herein falls in the range of about 0.01 mmoles/kg body weight of the subject/hour up to about 0.5 mmoles/kg/hr. Typical daily doses, in general, lie within the range of from about 10 $\mu$g up to about 100 mg per kg body weight, and, preferably within the range of from 50 $\mu$g to 10 mg per kg body weight and can be administered up to four times daily. The daily IV dose lies within the range of from about 1 $\mu$g to about 100 mg per kg body weight, and, preferably, within the range of from 10 $\mu$g to 10 mg per kg body weight.

In accordance with yet another embodiment of the present invention, there are provided improved methods for the treatment of a subject suffering from a pathological condition by administration thereto of pharmacologically active agent(s), the improvement comprising covalently attaching a dithiocarbamate disulfide to said pharmacologically active agent prior to administration thereof to said subject.

Thus, invention method for the treatment of a subject afflicted with a pathological condition comprises administering to a subject an effective amount of a modified pharmacologically active agent, wherein said pharmacologically active agent is effective for treatment of said condition, and wherein said pharmacologically active agent has been modified by the covalent attachment thereto of a dithiocarbamate disulfide.

The invention will now be described in greater detail by reference to the following non-limiting examples.

EXAMPLE 1

Synthesis of Disulfide Dithiocarbamates

1A Synthesis of N-Methyl-D-glucamine Dithiocarbamate Disulfide

To a solution of N-methyl-D-glucamine dithiocarbamate (MGD) (7.64 g or 26 mmol) in 30 ml water was added dropwise, under constant stirring with magnetic stirrer, a solution of iodine (3.3 g or 13 mmol) in 50 ml absolute ethanol. The iodine color disappeared immediately. An additional amount of ethanol (150 ml) was added at the end of the reaction. The reaction mixture was kept at 4° C. for four hours and the precipitate was filtered, washed with 2×50 mL ethanol and air dried for 24 hrs. After additional vacuum drying for 16 hrs, it produced 5.5 g of N-methyl-D-glucamine dithiocarbamate disulfide (MGDD). Yield 78%, the structure was confirmed by $^1$H NMR at 500 Mhz ($D_2O$) δ; 4.43 (2H, m); 4.35 (2H; m); 4.20 (1H, m); 4.04 (1H, m); 3.9–3.7 (12H, m); 3.7–3.6 (1H, m); 3.60 (3H, s) and by Mass analysis: calculated mass for $C_{16}H_{32}N_2O_{10}S_4$—($M+Na^+$): 563. Found: 563.

1B Synthesis of Pyrrolidine Dithiocarbamate Disulfide

To a solution of 3 g (18.3 mmol) pyrrolidine dithiocarbamate ammonium salt in 30 mL water is added with constant stirring to form a solution of 2.32 (9.1 mmol) iodine in 25 mL absolute ethanol. The reaction is very fast and the iodine color disappears instantly. At the end of the reaction, the product is filtered, washed with 3×20 mL water and dried overnight under vacuum. Yield 2.6 g (97%) of pyrrolidine dithiocarbamate disulfide. $^1$H NMR, 500 Mhz, ($CDCl_3$) δ; 3.88 (8H, m); 2.15 (4H; m); 2.02 (4H, m). Mass analysis: calculated for $C_{10}H_{16}N_2S_4$—(M+H)+: 293. Found: 393.

1C Synthesis of L-Proline Dithiocarbamate Disulfide

To a solution of L-proline dithiocarbamate (2.2 g or 9.46 mmol) in 40 mL water was added a solution of iodine (1.2 g or 4.7 mmol) in 17 mL absolute ethanol with constant stirring. The reaction reached completion within minutes as indicated by the disappearance of the iodine color. After the addition of acetone (180 ml), the product was crystallized in a few minutes. The product was filtered after two hours, then washed with 3×20 mL acetone and air dried overnight. Yield 1.7 g (85%) of L-Proline dithiocarbamate disulfide (L-PDD). The structure was confirmed by Mass analysis: calculated mass for $C_{12}H_{14}N_2Na_2O_4S_4$—($M+Na^+$): 447. Found: 447.

EXAMPLE 2

General Procedure for the Preparation of Dithiocarbamate Disulfide Conjugates with the Acetic Acid Derivatives of Nonsteroidal Anti-inflammatory Drugs (NSAIDs) (Scheme 1)

2A Procedure for the Preparation of Intermediate 3 (Scheme 1)

To a stirring solution of NSAID compound (1) (1 eq), diol compound (2) (5 eq) and dimethylaminopyridine (DMAP) (0.2 eq) in anhydrous THF were added 1,3-dicyclohexylcarbodiimide (DCC) (1 eq) at 0° C. The resulting solution was stirred at room temperature for several hours. The reaction solution was filtered and the solvent was evaporated. The residue was partially dissolved in ethyl acetate and the solid was filtered off and the solution was washed with 0.5 N HCl, saturated sodium bicarbonate solution and brine. After the solvent was evaporated, the compound was purified either by flash chromatography or recrystallization to give compound 3.

2B Procedure for the Preparation of Intermediate 5 (Scheme 1)

To a solution of compound 3 (1 eq) in pyridine was added p-toluenesulfonyl chloride (4) (2 eq) at 0° C. The resulting solution was put in the refrigerator (~4° C.) for three days. The reaction solution was poured onto ice and extracted with ether. The combined ether solution was washed with water and dried. After the solvent was evaporated, the residue was purified by an appropriate means to give compound 5.

2C Procedure for the Preparation of Conjugate Compound 7 (Scheme 1)

A solution of intermediate 5 and compound 6 in DMSO was stirred at room temperature under argon for one to three hours. The reaction solution was poured onto ice and extracted with ether. The combined ether solution was washed with water. The ether was dried and evaporated and the residue was purified to give the conjugate compound 7.

EXAMPLE 3

Synthesis of L-proline Dithiocarbamate Disulfide (PDD) Conjugates with Naproxen (PDD-Naproxen)

3A Synthesis of 3-Hydroxypropyl (S)-(+)-methoxy-α-methyl-2-naphthaleneacetate 10 (Scheme 2)

To a stirring solution of (S)-(+)-methoxy-α-methyl-2-naphthaleneacetic acid (naproxen, 8) (10.4 g, 45 mmol), propanediol (9) (17.1 g, 225 mmol) and DMAP (0.54 g, 4.5 mmol) in anhydrous THF (300 mL) was added DCC (9.4 g, 45 mmol) at 0° C. The resulting solution was stirred at 0° C. for 10 min and then at room temperature for 5 h. The reaction solution was filtered and the solvent was evaporated. The residue was partially dissolved in ethyl acetate and the solid was filtered off and the solution was washed with 0.5 N HCl, saturated sodium bicarbonate solution and brine. The organic phase was dried ($Na_2SO_4$) and the solvent was evaporated. The residue was purified by recrystallization from 1:3 hexanes-dichloromethane to give 9.7 g (75%) of compound 10 as a white solid; $^1$H NMR ($CDCl_3$) δ1.58 (d, 3H), 1.78 (m, 2H), 1.88 (t, 1H, ex $D_2O$), 3.53 (m, 2H), 3.87 (q, 1H), 3.90 (s, 3H), 4.2 (m, 2H), 7.11–7.39 (d, 1H), 7.65 (s, 1H), 7.70 (d, 2H); MS (ES) m/z 289.2 $(M+H)^+$ ($C_{17}H_{22}O_4$ requires 289.34).

3B Synthesis of 3-Tosylpropyl (S)-(+)-methoxy-α-methyl-2-naphthaleneacetate 11 (Scheme 2)

To a stirring solution of compound 10 (8.6 g, 30 mmol) in 35 mL of pyridine was added tosyl chloride (4) (11.43 g, 60 mmol) at 0° C. The resulting solution was put in refrigerator (~4° C.) for three days. The reaction solution was poured on to 300 g ice and extracted with ether. The combined ether solution was washed with 10% HCl solution, saturated $NaHCO_3$ solution and brine. The solution was dried ($Na_2SO_4$) and evaporated. The residue was purified by flash chromatography on a silica gel column using 100% $CH_2Cl_2$ as the eluent to give 8.92 g (67%) of compound 11 as a pale yellow oil; $^1$H NMR ($CDCl_3$) δ1.53 (d, 3H), 1.90 (m, 2H), 2.42 (s, 3H), 3.78 (q, 1H), 3.91 (s, 3H), 3.99 (m, 1H), 4.09 (t, 2H), 7.11–7.15 (m, 2H), 7.25–7.28 (m, 2H), 7.32–7.34 (m, 1H), 7.64 (m, 1H), 7.65–7.71 (m, 4H); MS (ES) m/z 443.3 (M+H)$^+$ (C$_{24}$H$_{27}$O$_6$S requires 443.53).

3C Synthesis of PDD-Naproxen (Compound 12; Scheme 2)

To a stirring solution of compound 11 (8.86 g, 20.02 mmol) in 35 mL of DMSO was added compound 6 (3.86 g, 9.1 mmol) at room temperature. The resulting solution was stirred at room temperature for 70 min. The reaction solution was poured on to 100 g ice and extracted with ether. The combined ether solution was washed with water and brine. The solution was dried (Na$_2$SO$_4$) and evaporated. The residue was purified by flash chromatography on a silica gel column using 200:1 and then 20:1 CH$_2$Cl$_2$—CH$_3$OH as eluents to give 3.74 g (45%) of compound 12 as a white foam; $^1$H NMR (CDCl$_3$) δ1.57(d, 6H), 1.94–2.20 (m, 12H), 3.20–3.25 (m, 4H), 3.57–3.59 (m, 2H), 3.72–3.79 (m, 2H), 3.84–3.88 (m, 2H), 3.90 (s, 6H), 5.05 (m, 2H), 7.10–7.14 (m, 4H), 7.39–7.41 (d, 2H), 7.65–7.70 (m, 6H); MS (ES) m/z 921.5 M$^+$ (C$_{46}$H$_{52}$N$_2$O$_{10}$S$_4$ requires 921.2).

EXAMPLE 4

Synthesis of L-proline Dithiocarbamate Disulfide (PDD) Conjugates with Ibuprofen (PDD-Ibuprofen)

4A Synthesis of 3-Hydroxypropyl (S)-(+)-4-isobutyl-α-methylphenylacetate 14 (Scheme 3)

Compound 14 was prepared as described above for compound 10 from (S)-(+)-4-isobutyl-A-methylphenylacetic acid (ibuprofen, 13) (4.12 g, 20 mmol) and propanediol (7.6 g, 100 mmol). The compound was purified by flash chromatography on a silica gel column using 10:1 and then 3:1 hexanes-ethyl acetate as eluents to give 3.54 g (65%) of compound 14 as a colorless oil; $^1$H NMR (CDCl$_3$) δ0.89 (d, 6H), 1.49 (d, 3H), 1.80 (m, 2H), 1.76–1.85 (m, 2H, 1H ex D$_2$O), 2.45 (m, 2H), 3.52 (m, 2H), 3.70 (q, 1H), 4.21 (m, 2H), 7.10 (d, 2H), 7.18 (d, 2H); MS (ES) m/z 265.7(M+H)$^+$ (C$_{16}$H$_{25}$O$_3$ requires 265.36).

4B Synthesis of 3-Tosylpropyl (S)-(+)-4-isobutyl-α-methylphenylacetate 15 (Scheme 3)

Compound 15 was prepared as described above for compound 11 from compound 14 (1.76 g, 0.56 mmol) and tosyl chloride (4) (0.5 g, 1.13 mmol). The compound was purified by flash chromatography on a silica gel column using CH$_2$Cl$_2$ as the eluent to give 1.5 g (54%) of the compound 15 as a colorless oil; $^1$H NMR (CDCl$_3$) δ0.88 (d, 6H), 1.43 (d, 3H), 1.80–1.92 (m, 3H), 2.44 (d, 2H), 2.45 (s, 3H), 3.61 (q, 1H), 3.99 (t, 2H), 4.08 (t, 2H), 7.07 (d, 2H), 7.13 (d, 2H), 7.33 (d, 2H) 7.75 (d, 2H); MS (ES) m/z 441.3 (M+Na)$^+$ (C$_{23}$H$_{30}$O$_5$SNa requires 441.55).

4C Synthesis of PDD-Ibuprofen (Compound 16; Scheme 3)

Compound 16 was prepared as described above for compound 12 from compound 15 (1.35 g, 3.2 mmol) and compound 6 (0.7 g, 1.6 mmol) in DMSO. The compound was purified by flash chromatography on a silica gel column using 200:1 and then 20:1 CH$_2$Cl$_2$—CH$_3$OH as eluents to give 0.55 g (40%) of compound 16 as a pale yellow oil; $^1$H NMR (CDCl$_3$) δ0.89 (d, 6H), 1.49 (d, 3H), 1.84 (m, 1H), 2.00 (m, 2H), 2.17–2.32 (m, 4H), 2.44 (d, 2H), 3.23 (m, 2H), 3.71 (m, 2H), 3.81 (m, 1H), 7.08 (d, 2H), 7.24 (d, 2H); MS (ES) m/z 873.2 M$^+$ (C$_{44}$H$_{60}$N$_2$O$_8$S$_4$ requires 873.22).

EXAMPLE 5

Synthesis of L-proline Dithiocarbamate Disulfide (PDD) Conjugates with Ketoprofen (PDD-ketoprofen)

A Synthesis of 3-Hyroxypropyl (S)-(+)-3-benzoyl-α-methylbenzeneacetate 18 (Scheme 4)

Compound 18 was synthesized as described above for compound 10 from (S)-(+)-3-benzoyl-α-methylbenzeneacetic acid (ketoprofen, 17) (3.8 g, 15 mmol) and propanediol (9) (5.7 g, 75 mmol). The compound was purified by flash chromatography on a silica gel column using 200:1 CH$_2$Cl$_2$—MeOH as the eluent to give 2.63 g (56%) of the compound 18 as a colorless oil; $^1$H NMR (CDCl$_3$) δ1.54 (d, 3H), 1.82 (m, 2H), 1.82–1.82 (b, 1H, ex D$_2$O), 3.58 (m, 2H), 3.79–3.83 (q, 1H), 4.25 (m, 2H), 7.42–7.80 (m, 9H); MS (ES) m/z 313.1 (M+H)$^+$ (C$_{19}$H$_{21}$O$_4$ requires 313.3).

5B Synthesis of 3-Tosylpropyl (S)-(+)-3-benzoyl-α-methylbenzeneacetate 19 (Scheme 4)

Compound 19 was synthesized as described above for compound 11 from compound 18 (2.48 g, 7.94 mmol) and compound 4 (3.03 g, 15.9 mmol). The compound was purified by flash chromatography on a silica gel column using 6:1 and then 4:1 hexanes-ethyl acetate as eluents to give 2.72 g (74%) of the compound 19 as a colorless oil; $^1$H NMR (CDCl$_3$) δ1.49 (d, 3H), 1.94 (m, 2H), 2.43 (s, 3H), 3.73 (q, 1H), 4.01 (t, 2H), 4.11 (t, 2H), 7.31–7.79 (m, 13H); MS (ES) m/z 467.3 (M+H)$^+$ (C$_{26}$H$_{27}$O$_6$S requires 467.55).

5C Synthesis of PDD-Ketoprofen (Compound 20; Scheme 4)

Compound 20 was prepared as described above for compound 12 from compound 6 (0.91 g, 2.15 mmol) and compound 19 (2.0 g, 4.30 mmol) in 9 ml of DMSO. The compound was purified by flash chromatography on a silica gel column using 3:1 hexanes-ethyl acetate and then 20:1 CH$_2$Cl$_2$—MeOH as eluents to give 1.21 g (58%) of the compound 20 as a pale yellow oil; $^1$H NMR (CDCl$_3$) δ1.44 (d, 3H), 1.82–2.11 (m, 6H), 3.12–3.28 (m, 2H), 3.59–3.72 (m, 2H), 3.61–3.75 (m, 2H), 3.90–4.15 (m, 3H), 4.85 (m, 1H), 7.51–7.73 (m, 9H); MS (ES) m/z 969.5 (M+H)$^+$ (C$_{50}$H$_{53}$N$_2$O$_{10}$S$_4$ requires 969.22).

EXAMPLE 6

Synthesis of L-proline Dithiocarbamate Disulfide (PDD) Conjugates with Indomethacin (PDD-Indomethacin)

6A Synthesis of 3-Hydroxypropyl 1-(p-chlorobenzoyl)-5-methoxy-2-methylindole-3-acetate 22 (Scheme 5)

Compound 22 was prepared as described above for compound 10 from 1-p-chlorobenzoyl)-5-methoxy-2-methylindole-3-acetic acid (indomethacin, 21) (1.8 g, 5.0 mmol) and propanediol (9) (1.9 g, 25 mmol). The compound was purified by flash chromatography on a silica gel column using 200:1, 100:1 and 50:1 CH$_2$Cl$_2$—MeOH as eluents to give 1.02 g (49%) of the compound 22 as a pale yellow oil; $^1$H NMR (CDCl$_3$) δ1.70 (t, 1H, ex D$_2$O), 1.86 (m, 2H), 2.39 (s, 3H), 3.63 (q, 2H), 3.68 (s, 2H), 3.84 (s, 3H), 4.27 (t, 2H), 6.67 (d, 1H), 6.86 (d, 1H), 6.95 (d, 1H), 7.48 (d, 2H), 7.66 (d, 2H); MS (ES) m/z 416.5 (M+H)$^+$ (C$_{22}$H$_{23}$ClNO$_5$ requires 416.87).

6B Synthesis of 3-Tosylpropyl 1-(p-chlorobenzoyl)-5-methoxy-2-methylindole-3-acetate 23 (Scheme 5)

Compound 23 was prepared as described above for compound 11 from compound 22 (0.96 g, 2.3 mmol) and compound 9 (0.88 g, 4.6 mmol). The compound was purified by flash chromatography on a silica gel column using 3:1 hexanes-ethyl acetate as the eluent to give 0.93 g (71%) of the compound 23 as a pale yellow oil; $^1$H NMR (CDCl$_3$) δ1.98 (m, 2H), 3.62 (s, 2H), 3.82 (s, 3H), 4.05 (t, 2H), 4.14 (t, 2H), 6.67 (d, 1H), 6.90 (d, 1H), 6.93 (d, 1H), 7.32 (d, 2H), 7.47 (d, 2H), 7.66 (d, 2H), 7.74 (d, 2H); MS (ES) m/z 592.0 (M+Na)$^+$ (C$_{29}$H$_{28}$ClNO$_7$SNa requires 592.13).

6C Synthesis of PDD-Indomethacin (Compound 24; Scheme 5)

Compound 24 was prepared as described above for compound 12 from compound 23 (0.89 g, 1.56 mmol) and compound 6 (0.33 g, 0.78 mmol). The compound was purified by flash chromatography on a silica gel column using 200:1 and then 20:1 $CH_2Cl_2$—MeOH as eluents to give 0.33 g (36%) of the compound 24 as a white foam; $^1$H NMR (CDCl$_3$) δ2.01–2.30 (m, 6H), 2.38 (s, 3H), 3.29 (t, 2H), 3.68 (m, 4H), 3.84 (s, 3H), 4.19 (t, 2H), 5.13 (t, 1H), 6.66 (m, 1H), 6.87 (d, 1H), 6.96 (d, 1H), 7.46 (d, 2H), 7.66 (d, 2H); MS (ES) m/z 1177.5 (M+H)$^+$ ($C_{54}H_{53}Cl_2N_4O_{12}S_4$ requires 1177.2).

EXAMPLE 7
Enzymatic Hydrolysis of PDD-NSAIDs

7A Enzymatic Hydrolysis of Compound 12

Compound 12 (4.6 mg, 0.0049 mmol) was dissolved in 0.25 ml of DMSO to make a 0.02M solution. The above solution (0.05 mL) was transferred to a 1 mL of PBS buffer and mixed with 33.3 units of the esterase. The resulting solution was put in a water bath (37° C.) for 30 min and then at room temperature overnight. The compound was decomposed into two compounds; Silica gel TLC $R_f$0.46 (naproxen) and $R_f$0.12 (20:1 $CH_2Cl_2$—MeOH).

7B Enzymatic Hydrolysis of Compound 16

Compound 16 was hydrolyzed as described above for compound 12. The compound 16 was decomposed into two compounds within 5 h; Silica gel TLC $R_f$0.64 (ibuprofen) and $R_f$0.12 (20:1 $CH_2Cl_2$—MeOH).

7C Enzymatic Hydrolysis of Compound 20

Compound 20 was hydrolyzed as described above for compound 12. The compound 20 was decomposed into two compounds within 5 h; Silica gel TLC $R_f$0.45 (ketoprofen) and $R_f$0.12 (20:1 $CH_2Cl_2$—MeOH).

7D Enzymatic Hydrolysis of Compound 24

Compound 24 was hydrolyzed as described above for compound 12. The compound 24 was decomposed into two compounds within 5 h; Silica gel TLC $R_f$0.44 (indomethacin) and $R_f$0.12 (20:1 $CH_2Cl_2$—MeOH).

EXAMPLE 8
Reduced Numbers of Gastric Erosions in the Rat Gastropathy Model by PDD-Naproxen The main side effect of NSAIDs is gastrointestinal ulceration and intolerance. Gastric damage from orally dosed NSAIDs has both local erosive and systemic ulcerative components. The ability to cause local erosions can be estimated by using the rat gastropathy model (Brand, S J et al. supra). Sprague-Dawley rats (male, 175–250 g), were food fasted overnight and then dosed orally with 5 to 10 ml/kg of drug, followed by removal of drinking water. After 2.5 hours, the rats were injected i.v. with Evans Blue to stain the gastric erosions. Thirty minutes later the animals were sacrificed by $CO_2$ inhalation and the stomachs removed, opened along the greater curvature, and washed with water. The total number of blue lesions was counted and the length of the lesions noted.

Figure 1:
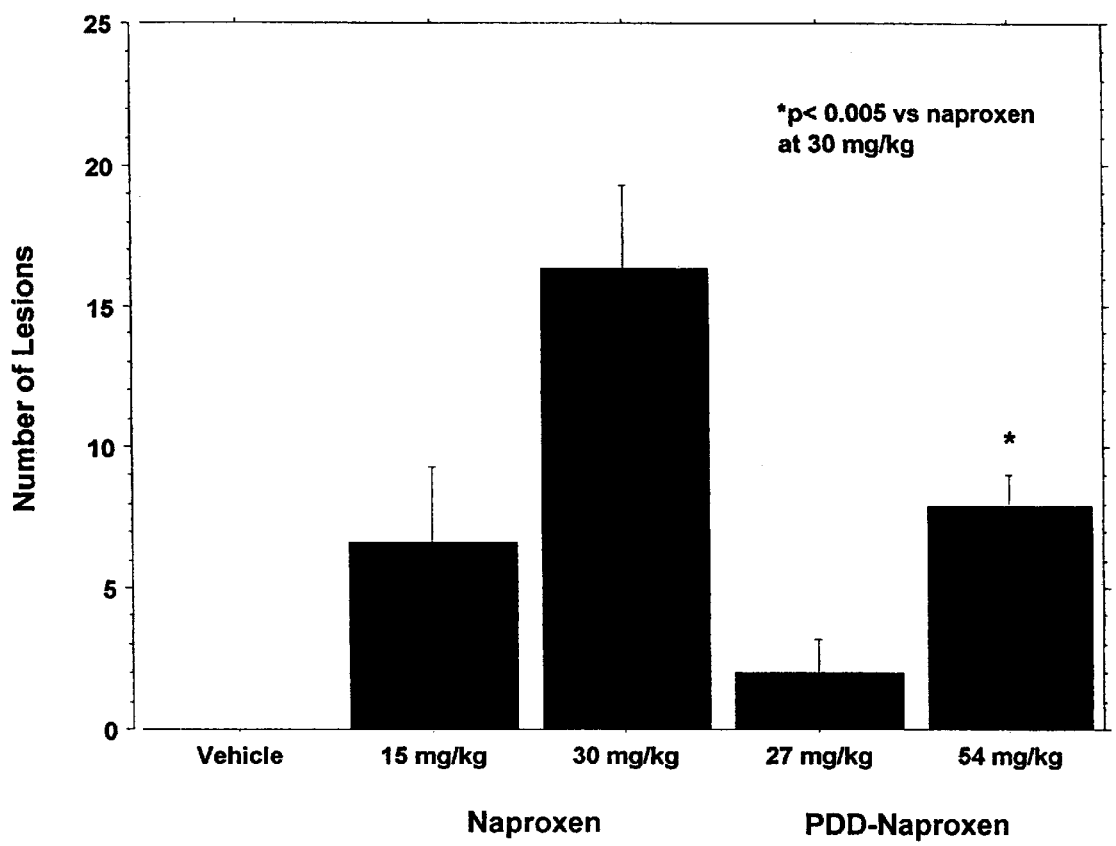
FIG. 1 illustrates the improved gastric safety of PDD-Naproxen (relative to unmodified Naproxen) in a rat model. The number of gastric lesions was measured three hours after oral dosing of fasted male Sprague-Dawley rats with vehicle, 2 different doses of naproxen or 2 different doses of a molar equivalent of PDD-Naproxen.

Administration of Naproxen at 15 and 30 mg/kg and equimolar doses of PDD-Naproxen (27 & 54 mg/kg) resulted in a dose-related number of lesions for both compounds (FIG. 1). Most of the lesions were linear or oval in shape and less than 2 mm in length; they were found primarily in the corpus of the stomach. The high dose PDD-Naproxen group had significantly fewer lesions than the high dose naproxen group (ANOVA; p<0.005). The low dose PDD-Naproxen group also showed fewer erosions than the low dose of naproxen, but statistical significance was not achieved with only 6 animals in each group. These results suggest that the naproxen prodrug, PDD-Naproxen, has the ability to reduce the number of erosions in the corpus of the stomach after oral administration in the rat.

EXAMPLE 9
Reduction of Acute Hindlimb Inflammation in the Rat Carrageenan-induced Hindlimb Edema Model by PDD-Naproxen Efficacy of NSAIDs in acute inflammation can be estimated by using intraplantar injection of carrageenan in the rat. Male Sprague-Dawley rats (200–250 g) were injected intradermally in the footpad with 50 μl of a 1% carrageenan solution in PBS. Swelling of the injected paw was measured at 2, 3, 5 & 7 hours using a plethysmometer.

Figure 3:
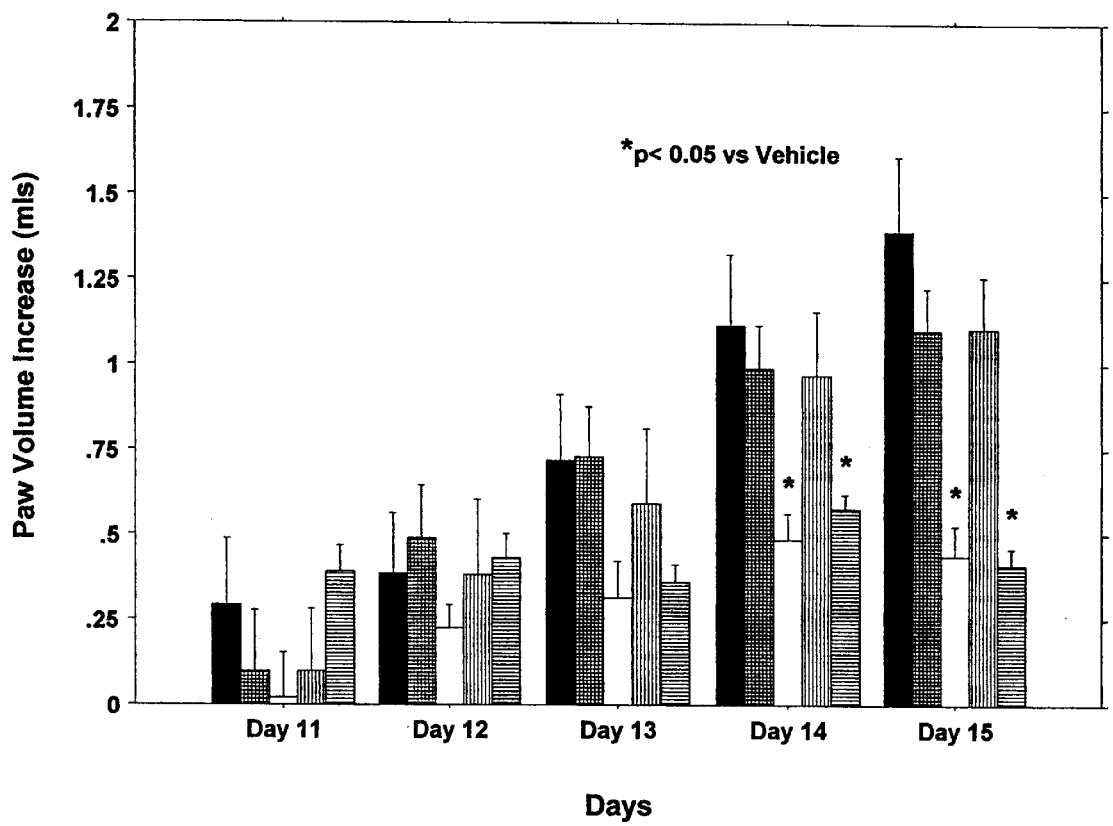
FIG. 3 illustrates the effectiveness of PDD-Naproxen in the treatment of adjuvant-induced arthritis in a rat model system. Thus, paw volume increases (measured with a Plethysmometer) are reported as a function of time, and were measured in the injected feet of Lewis male rats in which arthritis was induced by intradermel injection of adjuvant into the footpad. Rats were injected on day 0 and treated once orally with either vehicle, naproxen or PDD-Naproxen on days 5–8 and 11–14. Blackened boxes represent animals treated with vehicle (5% DMSO/CMC); checkered boxes represent animals treated with naproxen at 1 mg/kg, open boxes represent animals treated with naproxen at 10 mg/kg, vertically lined boxes represent animals treated with PDD-Naproxen at 1.8 mg/kg (molar equivalent of 1 mg/kg naproxen alone), and horizontally lined boxes represent animals treated with PDD-Naproxen at 18 mg/kg (molar equivalent of 10 mg/kg naproxen alone).

Pretreatment with oral naproxen given one hour before the carrageenan injection at 10 mg/kg resulted in a significant reduction in swelling that lasted from 2 to 5 hours post injection (FIG. 3). An equimolar dose of PDD-Naproxen (18 mg/kg) reduced inflammation significantly at 2 and 3 hours, but started to wear off by 5 hours. These results suggest that PDD-Naproxen is orally active in rats, but slightly less effective vs acute inflammation than the parent drug.

Conclusions: Oral PDD-Naproxen has antiinflammatory activity similar to naproxen in the chronic adjuvant arthritis and acute carrageenan hindlimb edema rat models. The tendency to cause gastric erosions is reduced in PDD-Naproxen. PDD-Naproxen may be an effective prodrug form of naproxen with reduced gastric side effects.

EXAMPLE 10
Reduction of Chronic Hindlimb Inflammation in the Rat Adjuvant Arthritis Model by PDD-Naproxen NSAIDs are useful in both chronic and acute inflammatory conditions. Efficacy in chronic inflammation can be estimated using the rat adjuvant arthritis model (Blackham et al. supra). In this model Lewis male rats (175–250 g) were injected intradermally in the footpad with M. tuberculosis powder suspended in mineral oil at 5 mg/ml. Progressive swelling of the uninjected paw and ankle joint between days 11 and 15 was measured by plethysmometry.

Figure 2:
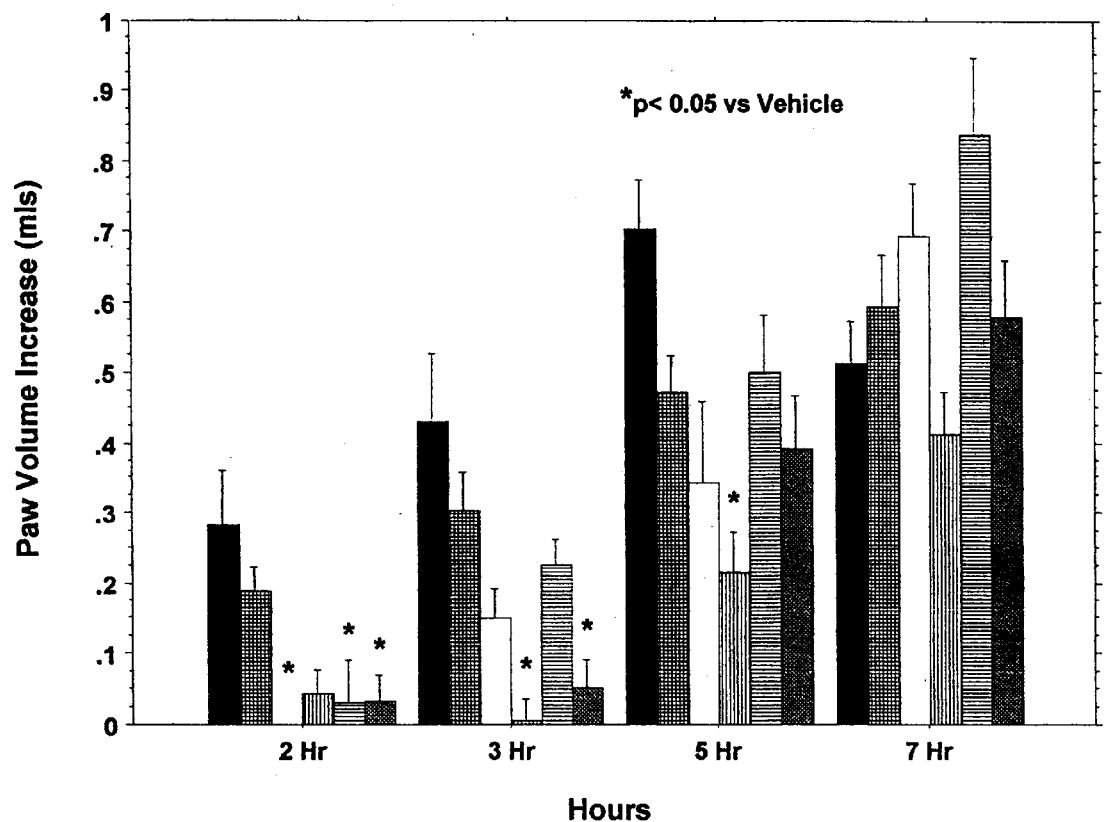
FIG. 2 illustrates the alleviation of acute inflammation by PDD-Naproxen in a carrageenen model in rats. Paw volume increases (measured with a Plethysmometer) are reported as a function of time, and were measured on the injected feet of male Sprague-Dawley rats which had been pretreated at −1 hour with oral vehicle, naproxen or PDD-Naproxen, then injected transdermally with 1% carrageenen. Blackened boxes represent untreated animals, checkered boxes represent animals to whom vehicle (5% DMSO/CMC) was administered, open boxes represent naproxen administration at 3 mg/kg, vertically lined boxes represent naproxen administration at 10 mg/kg, horizontally lined boxes represent PDD-Naproxen administration at 5.5 mg/kg (molar equivalent of 3 mg/kg naproxen alone), and diagonally cross-hatched boxes represent PDD-Naproxen at 18 mg/kg (molar equivalent of 10 mg/kg naproxen alone).

Rats were dosed daily by by oral gavage with 5 ml/kg of naproxen at 1 and 10 mg/kg and equimolar doses of NOX-319 (1.8 and 18 mg/kg) on days 5–8 and 11–14. The high doses of both drugs produced a comparable reduction of swelling on days 13 through 15 (FIG. 2), with a reduction compared to control of approximately 70% by day 15. The lower doses also appeared to have a slight effect by day 15. The results show that equimolar doses of PDD-Naproxen resulted in antiinflammatory effects equal to those of naproxen in this model.

EXAMPLE 11
Pharmacokinetics of Naproxen in Plasma Following Intravenous Administration of PDD-Naproxen or Naproxen in Rats Naproxen is a nonsteroidal anti-inflammatory drug (NSAID) that is widely used in the treatment of rheumatoid arthritis, osteoarthritis, juvenile arthritis, ankylosing spondylitis, tendinitis and bursitis, and acute gout. Naproxen sodium, the sodium salt of naproxen, has also been developed as an analgesic because it is more rapidly absorbed. The side effects of GI ulceration, bleeding, and perforation is problematic to naproxen and NSAID therapy in general. Therefore, any therapeutic approach that decreases the side effects of naproxen could widen the usage of this therapy in treating inflammatory diseases.

The test articles utilized were PDD-Naproxen (Medinox, Inc., San Diego) stored as a powder (at 4° C.) and naproxen (Sigma, St. Louis) stored at room temperature. On the day of animal dosing, test articles were freshly prepared in the mixture of carboxymethylcellulose (Sigma, St. Louis) and dimethylsulfoxide (Sigma, St. Louis) or water for injection.

Rats were catheterized using the carotid artery and jugular vein. The catheters were flushed with 30% polyvinylpyrrolidone (400 U/mL of heparin) to prevent clotting in the tip. 250 μL blood samples were collected by unhooking the flush syringe and letting the blood flow freely into centrifuge tubes at predetermined time points (see Table 1). The tubes were centrifuged at 13,000 rpm for 10 min at 40° C. All plasma samples were analyzed for naproxen content on the same day of collection.

A 50 μL aliquot of plasma sample was mixed with 100 μL of acetonitrile. After vortexing and centrifugation, 100 μL of supernatant was collected and added to 150 μL of 50 mM phosphate buffer (pH 5.0). After vortexing and centrifugation, 25 μL of supernatant was analyzed for naproxen by HPLC using a UV detector.

Pharmacokinetic analysis: The average plasma concentration at each time point was calculated and utilized in a pharmacokinetic analysis. Compartmental or noncompartmental pharmacokinetic analyses were performed using the WinNonlin program to calculate the following parameters: maximum concentration at 2 minutes ($C_{max}$), time to maximum concentration ($T_{max}$), area under the curve from zero to the last time point ($AUC_{last}$), area under the curve from zero to infinite time ($AUC_{inf}$), terminal phase half life (Beta-$t_{1/2}$), total plasma clearance (CL), and volume distribution at steady state ($V_{ss}$).

TABLE 1

Rat group assignment and doses

| Test Article | Group # | Rat # | Dose (mg/kg) | Plasma Sample Time |
|---|---|---|---|---|
| Naproxen | 2 | 1, 2, 3, & 4 | IV (0.55 mg/kg) | 5 min, 0.5, 1, 2, 3, 4, 5, 6, 7, & 8 hrs |
| PDD-Naproxen | 1 | 1, 2, 3, & 4 | IV (1 mg/kg) | 5 min, 0.5, 1, 2, 3, 4, 5, 6, 7, & 8 hrs |

Note that 1 mg of PDD-Naproxen prodrug contains 0.55 mg of naproxen.

Figure 4:
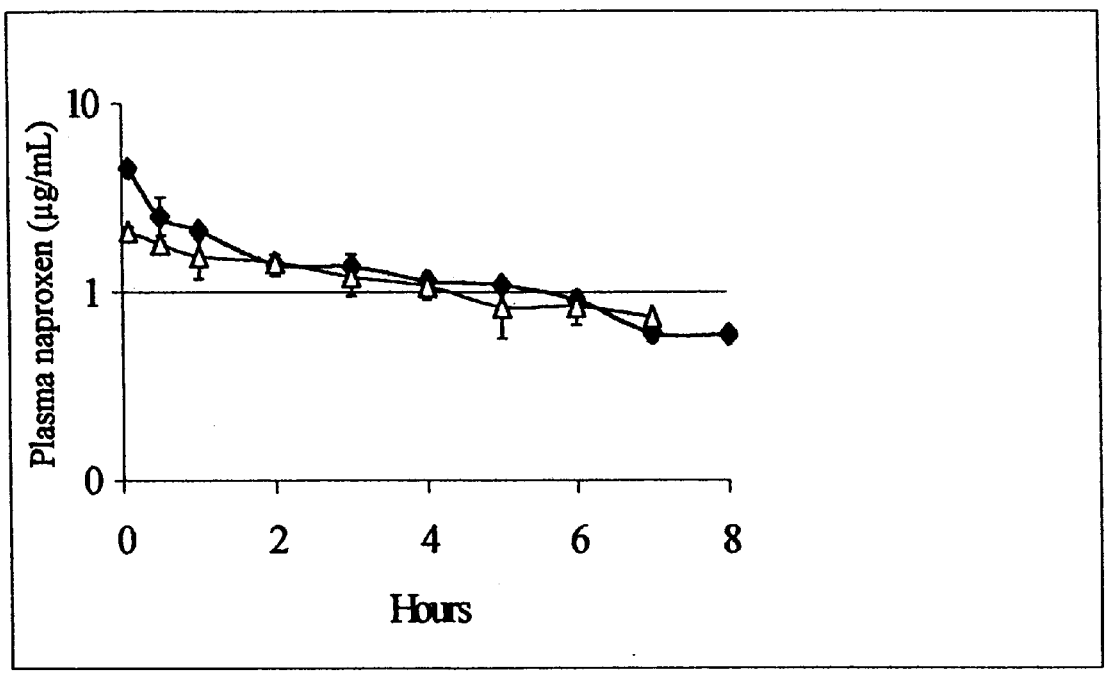
FIG. 4 presents concentration versus time curves for naproxen following IV administration of naproxen or PDD-Naproxen. Blackened rectangles represent plasma concentration of naproxen following IV administration of 0.55 mg/kg of naproxen and open triangles represent plasma concentration of naproxen following IV administration of 1.1 mg/kg of PDD-Naproxen. After IV administration of naproxen, the naproxen plasma concentrations declined in a bi-exponential manner.

FIG. 4 presents the naproxen plasma concentration-time curves. After IV administration of naproxen, the naproxen plasma concentrations declined with bi-exponential manner, while the decline of PDD-Naproxen was monophasic. Table 2 shows the naproxen pharmacokinetic parameters. Both sets of pharmacokinetic parameters were similar except (5.39 and 1.98 μg/mL for naproxen and PDD-Naproxen administration, respectively). This slow release of naproxen from PDD-Naproxen might be advantageous in helping to reduce naproxen's side effects by slowing the rise of plasma $C_{max}$. In addition, the results show clearly that when administered intravenously, naproxen is released from PDD-Naproxen and appears in the circulation.

TABLE 2

Naproxen plasma pharmacokinetic parameters (n = 4, pooled data) after IV administration of PDD-Naproxen or naproxen in rats (compartmental analysis)

| Drug | Amount (mg/kg) | $C_{max}$ (μg/mL) | $AUC_{all}$ (μ*min/mL) | $AUC_{inf}$ (μ*min/mL) | $t_{½}$ (hrs) | CL (mL/hr*kg) | $V_{ss}$ (L/kg) |
|---|---|---|---|---|---|---|---|
| Naproxen | 0.55 | 5.39 | N/A | 14.60 | 4.36 | 38 | 0.22 |
| PDD-Naproxen | 1.00 | 1.98 | N/A | 12.70 | 4.44 | 43 | 0.28 |

EXAMPLE 12
Plasma Pharmacokinetics of Naproxen Following Oral Administration of PDD-Naproxen or Naproxen in Rats The cannulated rats were separated into two groups as shown in Table 3. After oral gavage, the blood samples were withdrawn in various time points (Table 3) for HPLC analysis of naproxen levels.

TABLE 3

Rat group assignment and doses

| Test Article | Group # | Rat # | Dose (mg/kg) | Plasma Sample Time |
|---|---|---|---|---|
| Naproxen | 2 | 5, 6, 7, & 8 | oral (2.2 mg/kg) | 0.25, 0.5, 1, 3, 5, 7, 9, 11, 13 & 14 hrs |
| PDD-Naproxen | 1 | 1, 2, 3, & 4 | oral (4 mg/kg) | 0.25, 0.5, 1, 3, 5, 7, 9, 11, 13 & 14 hrs |

Note that 4 mg of the PDD-Naproxen prodrug contains 2.2 mg of naproxen.

FIG. 5 presents the naproxen plasma concentration-time curves. Following oral administration of PDD-Naproxen, the time to maximum naproxen plasma levels was considerably delayed compared to naproxen ($T_{max}$ of 1.3 and 6.4 hours for PDD-Naproxen and naproxen, respectively) (Table 4). The corresponding $C_{max}$ values were 2.34 and 4.05 a μg/mL, respectively. There was no significant difference for $AUC_{inf}$ values. The lower $C_{max}$, longer $T_{max}$, and similar $AUC_{inf}$ of PDD-Naproxen could be significant factors in reducing the side effects of naproxen.

TABLE 4

Naproxen plasma pharmacokinetic parameters (n = 4, pooled data) after oral administration of PDD-Naproxen or naproxen in rats (compartmental analysis)

| Drug | Dose (mg/kg) | $C_{max}$ (μg/mL) | $T_{max}$ (hrs) | $AUC_{all}$ (μg*hr/mL) | $AUC_{inf}$ (μg*hr/mL) | $t_{½}$ (hrs) |
|---|---|---|---|---|---|---|
| Naproxen | 2.2 | 4.82 | 1.3 | N/A | 48.4 | 6.0 |
| PDD-Naproxen | 4 | 2.34 | 6.4 | N/A | 45.6 | 7.5 |

Based on plasma data, PDD-Naproxen by oral or IV administration, produces better naproxen pharmacokinetic profiles than naproxen itself.

While the invention has been described in detail with reference to certain preferred embodiments thereof, it will be understood that modifications and variations are within the spirit and scope of that which is described and claimed.

That which is claimed is:

1. A method for the in vivo reduction of free radical levels in a subject, said method comprising administering to the subject an effective amount of a composition comprising
   i. a pharmaceutically acceptable carrier,
   ii. a compound having the structure (I) as follows:

$$R_1R_2N-C(S)-S-S-(S)C-NR_2R_1 \quad (I)$$

wherein:
   each of $R_1$ and $R_2$ is independently selected from a $C_1$ up to $C_{18}$ alkyl, substituted alkyl, a cycloalkyl, a substituted cycloalkyl, heterocyclic, a substituted heterocyclic, an alkenyl, a substituted alkenyl, an alkynyl, a substituted alkynyl, an aryl, a substituted aryl, an heteroaryl, a substituted heteroaryl, an alkylaryl, a substituted alkylaryl, an arylalkyl, and a substituted arylalkyl, or
   wherein $R_1$ and $R_2$ cooperate to form a 5-, 6- or 7-membered ring including N, $R_1$ and $R_2$ or
   $R_1$ or $R_2$ is a divalent moiety selected from the group consisting of an alkylene, a substituted alkylene, an oxyalkylene, a substituted oxyalkylene, an alkenylene, a substituted alkenylene, an arylene, a substituted arylene, an alkarylene, a substituted alkarylene, an aralkylene and a substituted aralkylene, wherein said divalent moiety serves as the same substituent for two dithiocarbamate structures, thereby linking said structures together so as to form a bis(dithiocarbamate), and
   iii. optionally, a reducing agent to reduce the disulfide bond in the dithiocarbamate,
   wherein the composition is administered so as to bind free radicals in the subject.

2. A method according to claim 1, wherein:
   each of $R_1$ and R2=a $C_1$ up to $C_{12}$ alkyl, substituted alkyl, alkenyl, substituted alkenyl, alkynyl, or substituted alkynyl, wherein the substituents are selected from carboxyl, —C(O)H, oxyacyl, phenol, phenoxy, pyridinyl, pyrrolidinyl, amino, amido, hydroxy, nitro, or sulfuryl, or
   $R_1$ and $R_2$ cooperate to form a 5-, 6-, or 7-membered ring including N, $R_1$, and $R_2$.

3. A method according to claim 1, wherein:
   $R_1$ is selected from a $C_2$ up to $C_8$ alkyl or substituted alkyl, wherein the substituents are selected from carboxyl, acetyl, pyridinyl, pyrrolidinyl, amino, amido, hydroxy, or nitro, and
   $R_2$ is selected from a $C_1$ up to $C_6$ alkyl or substituted alkyl, or
   $R_2$ cooperates with $R_1$ to form a 5-, 6-, or 7-membered ring including N, $R_1$, and $R_2$.

4. A method according to claim 1, wherein:
   $R_1$ is selected from a $C_2$ up to $C_8$ alkyl or substituted alkyl, wherein the substituents are selected from carboxyl, acetyl, amido, or hydroxy, and
   $R_2$ is selected from a $C_1$ up to $C_4$ alkyl or substituted alkyl, or
   $R_2$ cooperates with $R_1$ to form a 5-, 6-, or 7-membered ring including N, $R_1$, and $R_2$.

5. A method according to claim 1, wherein:
   $R_1$ and $R_2$ cooperate to form a 5-, 6-, or 7-membered ring, and the combination of $R_1$ and $R_2$ is selected from the group consisting of a saturated or unsaturated 4, 5, or 6 atom bridging species selected from the group consisting of alkylene, alkenylene, —O—, —S—, —C(O)—, and —N(R)-containing alkylene moieties, wherein R is hydrogen or a lower alkyl moiety.

6. A method according to claim 5, wherein said compound is pyrrolidine dithiocarbamate or proline dithiocarbamate.

7. A method according to claim 1, wherein said pharmaceutically acceptable carrier is selected from a solid, solution, emulsion, dispersion, micelle, or liposome.

8. A method according to claim 7, wherein said pharmaceutically acceptable carrier comprises an enteric coating.

9. A method according to claim 1, wherein said free radical levels are associated with a disease state selected from the group consisting of septic shock, ischemia, administration of cytokines, overexpression of cytokines, ulcers, gastritis, ulcerative colitis, Crohn's disease, diabetes, rheumatoid arthritis, asthma, Alzheimer's disease, Parkinson's disease, multiple sclerosis, cirrhosis, allograft rejection, transplant rejection, encephalomyelitis, meningitis, pancreatitis, peritonitis, vasculitis, lymphocytic choriomeningitis, glomerulonephritis, uveitis, glaucoma, blepharitis, chalazion, allergic eye disease, corneal ulcer, keratitis, cataract, retinal disorders, age-related macular degeneration, optic neuritis ileitis, inflammation induced by overproduction of inflammatory cytokines, hemorrhagic shock, anaphylactic shock, burn, infection leading to the overproduction of inflammatory cytokines induced by bacteria, virus, fungus, and parasites, hemodialysis, chronic fatigue syndrome, stroke, cancers, cardiovascular diseases associated with overproduction of inflammatory cytokines, heart disease, cardiopulmonary bypass, ischemic/reperfusion injury, ischemic/reperfusion associated with overproduction of inflammatory cytokines, toxic shock syndrome, adult respiratory distress syndrome, cachexia, myocarditis, autoimmune disorders, eczema, psoriasis, heart failure, dermatitis, urticaria, cerebral ischemia, systemic lupus erythematosis, AIDS, AIDS dementia, chronic neurodegenerative disease, chronic pain, priapism, cystic fibrosis, amyotrophic lateral sclerosis, schizophrenia, depression, premenstrual syndrome, anxiety, addiction, migraine, Huntington's disease, epilepsy, gastrointestinal motility disorders, obesity, hyperphagia, neuroblastoma, malaria, hematologic cancers, myelofibrosis, lung injury, graft-versus-host disease, head injury, CNS trauma, hepatitis, renal failure, g., chronic hepatitis C, paraquat), transplant rejection and preservation, fertility enhancement, bacterial translocation, circulatory shock, traumatic shock, hemodialysis, hangover, and combinations of two or more thereof.

* * * * *